US012567506B2

(12) United States Patent
Shelton, IV et al.

(10) Patent No.: US 12,567,506 B2
(45) Date of Patent: Mar. 3, 2026

(54) SIMULATION-BASED SURGICAL PROCEDURE PLANNING SYSTEM

(71) Applicant: Cilag GmbH International, Zug (CH)

(72) Inventors: Frederick E. Shelton, IV, Hillsboro, OH (US); Charles J. Scheib, Loveland, OH (US); Dwight Alan Meglan, Westwood, MA (US); Kevin M. Fiebig, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 736 days.

(21) Appl. No.: 17/332,197

(22) Filed: May 27, 2021

(65) Prior Publication Data

US 2022/0370131 A1     Nov. 24, 2022

Related U.S. Application Data

(60) Provisional application No. 63/191,681, filed on May 21, 2021.

(51) Int. Cl.
G16H 50/50     (2018.01)
A61B 18/14     (2006.01)
(Continued)

(52) U.S. Cl.
CPC ............. G16H 50/50 (2018.01); A61B 18/14 (2013.01); A61B 34/25 (2016.02); A61B 34/30 (2016.02);
(Continued)

(58) Field of Classification Search
CPC ........ G06N 20/00; G16H 50/00–50/80; G16H 20/40; A61B 34/10–2034/108
See application file for complete search history.

(56) References Cited

U.S. PATENT DOCUMENTS

| 8,311,791 | B1 | 11/2012 | Avisar |
| 9,104,791 | B2 | 8/2015 | Cohen et al. |

(Continued)

FOREIGN PATENT DOCUMENTS

| CN | 110638529 A | 1/2020 |
| DE | 102015208804 A1 | 11/2016 |

(Continued)

OTHER PUBLICATIONS

Gallagher, A. et al., "Fundamentals of Surgical Simulation", Gallagher, et al., "Fundamentals of Surgical Simulation, Principles and Practices Improving Medical Outcome-Zero Tolerance", DOI 10.1007/ 978-0-85729-763-1_12, © Springer-Verlag London Limited 2012, 384 pages.

(Continued)

*Primary Examiner* — Jonathan T Kuo
(74) *Attorney, Agent, or Firm* — Condo Roccia Koptiw LLP

(57) ABSTRACT

A computing device for generating a surgical procedure plan via surgical simulation may include a processor. The processor may be configured to obtain an indication of a surgical task. The surgical task may be associated with a surgical step of the surgical procedure plan. The processor may be configured to obtain a surgical choice and a corresponding predicted surgical outcome. The surgical choice and the corresponding predicted surgical outcome may be associated with the surgical task. The processor may be configured to generate a visualization of the surgical choice and the corresponding predicted surgical outcome in a simulated environment. The processor may be configured to obtain an indication of the surgical choice being selected. The processor may be configured to store the surgical choice in the surgical procedure plan.

16 Claims, 21 Drawing Sheets

(51) Int. Cl.

| | |
|---|---|
| *A61B 34/00* | (2016.01) |
| *A61B 34/30* | (2016.01) |
| *A61B 34/37* | (2016.01) |
| *A61B 90/00* | (2016.01) |
| *G06F 30/20* | (2020.01) |
| *G06N 20/00* | (2019.01) |
| *G06N 20/10* | (2019.01) |
| *G09B 9/00* | (2006.01) |
| *G09B 19/00* | (2006.01) |
| *G09B 23/30* | (2006.01) |
| *G16H 15/00* | (2018.01) |
| *G16H 20/40* | (2018.01) |
| *G16H 30/40* | (2018.01) |
| *G16H 40/20* | (2018.01) |
| *G16H 40/63* | (2018.01) |
| *G16H 40/67* | (2018.01) |
| *G16H 50/70* | (2018.01) |
| *G16H 70/20* | (2018.01) |
| *A61B 18/12* | (2006.01) |
| *A61B 34/10* | (2016.01) |

(52) U.S. Cl.

CPC .............. *A61B 34/37* (2016.02); *A61B 90/36* (2016.02); *G06F 30/20* (2020.01); *G06N 20/00* (2019.01); *G06N 20/10* (2019.01); *G09B 9/00* (2013.01); *G09B 19/003* (2013.01); *G09B 23/30* (2013.01); *G16H 15/00* (2018.01); *G16H 20/40* (2018.01); *G16H 30/40* (2018.01); *G16H 40/20* (2018.01); *G16H 40/63* (2018.01); *G16H 40/67* (2018.01); *G16H 50/70* (2018.01); *G16H 70/20* (2018.01); *A61B 2018/1253* (2013.01); *A61B 2018/126* (2013.01); *A61B 34/10* (2016.02); *A61B 2034/101* (2016.02); *A61B 2034/102* (2016.02); *A61B 2034/105* (2016.02); *A61B 2034/107* (2016.02); *A61B 2034/252* (2016.02); *A61B 2034/254* (2016.02); *A61B 2034/256* (2016.02); *A61B 2034/258* (2016.02); *A61B 2090/363* (2016.02); *A61B 2090/365* (2016.02); *A61B 2218/002* (2013.01); *A61B 2218/008* (2013.01)

(56) References Cited

U.S. PATENT DOCUMENTS

| | | | |
|---|---|---|---|
| 9,734,632 B2 * | 8/2017 | Thomas ................. | A61B 34/10 |
| 9,747,493 B2 | 8/2017 | Rodriguez et al. | |
| 9,875,339 B2 | 1/2018 | Namer Yelin et al. | |
| 9,881,520 B2 | 1/2018 | Ullrich et al. | |
| 10,172,676 B2 | 1/2019 | Ecabert et al. | |
| 2005/0196737 A1 | 9/2005 | Mann | |
| 2008/0235052 A1 | 9/2008 | Node-Ianglois et al. | |
| 2009/0089092 A1 | 4/2009 | Johnson et al. | |
| 2009/0112538 A1 * | 4/2009 | Anderson ............. | G06Q 10/06 |
| | | | 703/6 |
| 2009/0177454 A1 | 7/2009 | Bronstein et al. | |
| 2009/0202972 A1 | 8/2009 | Adhami et al. | |
| 2010/0178644 A1 | 7/2010 | Meglan et al. | |
| 2012/0016691 A1 | 1/2012 | Sievenpiper et al. | |
| 2012/0197619 A1 | 8/2012 | Namer et al. | |
| 2014/0272866 A1 | 9/2014 | Kim | |
| 2015/0005622 A1 | 1/2015 | Zhao et al. | |
| 2015/0088547 A1 | 3/2015 | Balram et al. | |
| 2016/0314710 A1 | 10/2016 | Jarc et al. | |
| 2017/0148213 A1 * | 5/2017 | Thomas ................. | A61B 34/20 |
| 2017/0181808 A1 | 6/2017 | Panescu et al. | |
| 2017/0319283 A1 | 11/2017 | Suresh et al. | |
| 2018/0060455 A1 | 3/2018 | Castillo | |
| 2018/0098813 A1 | 4/2018 | Nesichi et al. | |

| | | | |
|---|---|---|---|
| 2018/0116724 A1 | 5/2018 | Gmeiner et al. | |
| 2018/0247558 A1 | 8/2018 | Livneh | |
| 2018/0344308 A1 | 12/2018 | Nawana et al. | |
| 2018/0348876 A1 | 12/2018 | Banerjee et al. | |
| 2019/0000578 A1 * | 1/2019 | Yu .......................... | A61B 34/10 |
| 2019/0059997 A1 | 2/2019 | Frushour | |
| 2019/0125361 A1 | 5/2019 | Shelton, IV et al. | |
| 2019/0200844 A1 | 7/2019 | Shelton, IV et al. | |
| 2019/0201118 A1 | 7/2019 | Shelton, IV et al. | |
| 2019/0201137 A1 | 7/2019 | Shelton, IV et al. | |
| 2019/0201140 A1 | 7/2019 | Yates et al. | |
| 2019/0206564 A1 | 7/2019 | Shelton, IV et al. | |
| 2019/0206569 A1 | 7/2019 | Shelton, IV et al. | |
| 2019/0206576 A1 | 7/2019 | Shelton, IV et al. | |
| 2019/0272917 A1 | 9/2019 | Couture et al. | |
| 2019/0325574 A1 | 10/2019 | Jin et al. | |
| 2019/0362651 A1 | 11/2019 | Barral et al. | |
| 2019/0380792 A1 | 12/2019 | Poltaretskyi et al. | |
| 2020/0118691 A1 | 4/2020 | Kiljanek | |
| 2020/0174451 A1 | 6/2020 | Chanin | |
| 2020/0237452 A1 | 7/2020 | Wolf et al. | |
| 2020/0242686 A1 | 7/2020 | García Giraldez et al. | |
| 2020/0273581 A1 * | 8/2020 | Wolf ...................... | G16H 40/63 |
| 2020/0275976 A1 | 9/2020 | Mckinnon et al. | |
| 2020/0405403 A1 | 12/2020 | Shelton, IV et al. | |
| 2021/0137634 A1 | 5/2021 | Lang | |
| 2021/0142497 A1 | 5/2021 | Pugh et al. | |
| 2022/0233119 A1 | 7/2022 | Shelton, IV et al. | |
| 2022/0370132 A1 | 11/2022 | Shelton, IV et al. | |
| 2022/0370133 A1 | 11/2022 | Scheib et al. | |
| 2022/0370134 A1 | 11/2022 | Shelton, IV et al. | |
| 2022/0370135 A1 | 11/2022 | Shelton, IV et al. | |
| 2022/0370136 A1 | 11/2022 | Scheib et al. | |
| 2022/0370137 A1 | 11/2022 | Shelton, IV et al. | |
| 2022/0370138 A1 | 11/2022 | Shelton, IV et al. | |
| 2022/0375570 A1 | 11/2022 | Shelton, IV et al. | |
| 2022/0375620 A1 | 11/2022 | Scheib et al. | |
| 2022/0384022 A1 | 12/2022 | Matsuura et al. | |
| 2023/0293236 A1 | 9/2023 | Wright et al. | |

FOREIGN PATENT DOCUMENTS

| | | |
|---|---|---|
| EP | 2269693 A1 | 1/2011 |
| EP | 3367387 A1 | 8/2018 |
| EP | 3506290 A1 | 7/2019 |
| EP | 3649994 A1 | 5/2020 |
| JP | 2021509034 A | 3/2021 |
| KR | 101940706 B1 | 4/2019 |
| WO | 2011108994 A1 | 9/2011 |
| WO | 2017/027638 A1 | 2/2017 |
| WO | 2020072255 A1 | 4/2020 |
| WO | 2020163358 A1 | 8/2020 |

OTHER PUBLICATIONS

Andersen et al., "Augmented Visual Instruction for Surgical Practice and Training", IEEE Workshop on Virtual and Augmented Realities for Good; Reutlingen, Germany, Mar. 18, 2018, 5 pages.

Elhelw, Mohamed A., "Overview of Surgical Simulation", Center for Informatics Science, Nile University, Giza, Egypt, May 2020, 26 pages.

Reiter et al., "Surgical Structured Light for 3D Minimally Invasive Surgical Imaging", IEEE/RSJ International Conference on Intelligent Robot and Systems(IROS 2014), Chicago, IL, Sep. 14-18, 2014, pp. 1282-1287.

Wang et al., "High Resolution Acquisition, Learning, and Transfer of Dynamic 3-D Facial Expressions", Eurographics, vol. 23, No. 3, 2004, pp. 677-686.

International Search Report and Written Opinion received for PCT Application No. PCT/IB2022/054724, Mailed on Jul. 5, 2022, 13 pages.

International Search Report and Written Opinion received for PCT Application No. PCT/IB2022/054738, Mailed on Jul. 14, 2022, 14 pages.

International Search Report and Written Opinion received for PCT Application No. PCT/IB2022/054739, Mailed on Jul. 18, 2022, 13 pages.

(56)         References Cited

OTHER PUBLICATIONS

International Search Report and Written Opinion received for PCT Application No. PCT/IB2022/054725, Mailed on Jul. 8, 2022, 11 pages.
Ben-Hamadou et al., "Construction of Extended 3D Field of Views of the Internal Bladder Wall Surface: A Proof of Concept", 3D Research, 3D Display Research Center, Seoul, vol. 7, No. 19, Jul. 16, 2016, pp. 1-19.
Bernhardt et al., "The Status of Augmented Reality in Laparoscopic Surgery as of 2016", Medical Image Analysis, vol. 37, Apr. 1, 2017, pp. 66-90.
ISO 26262-1, "Road Vehicles—Functional Safety—Part 1: Vocabulary", International Organization for Standardization, Edition 2, Dec. 2018, 13 pages.

* cited by examiner

102

33150

Obtain an indication of a surgical task

33152

Obtain a surgical choice and a corresponding predicted surgical outcome

33154

Generate a visualization of the surgical choice and the corresponding predicted surgical outcome

33156

Obtain an indication of the surgical choice being selected

33158

Store the surgical choice in the surgical procedure plan

33160

ML assisted simulation driven tool-tissue interaction assessment – Goal is avoiding tissue manipulation errors

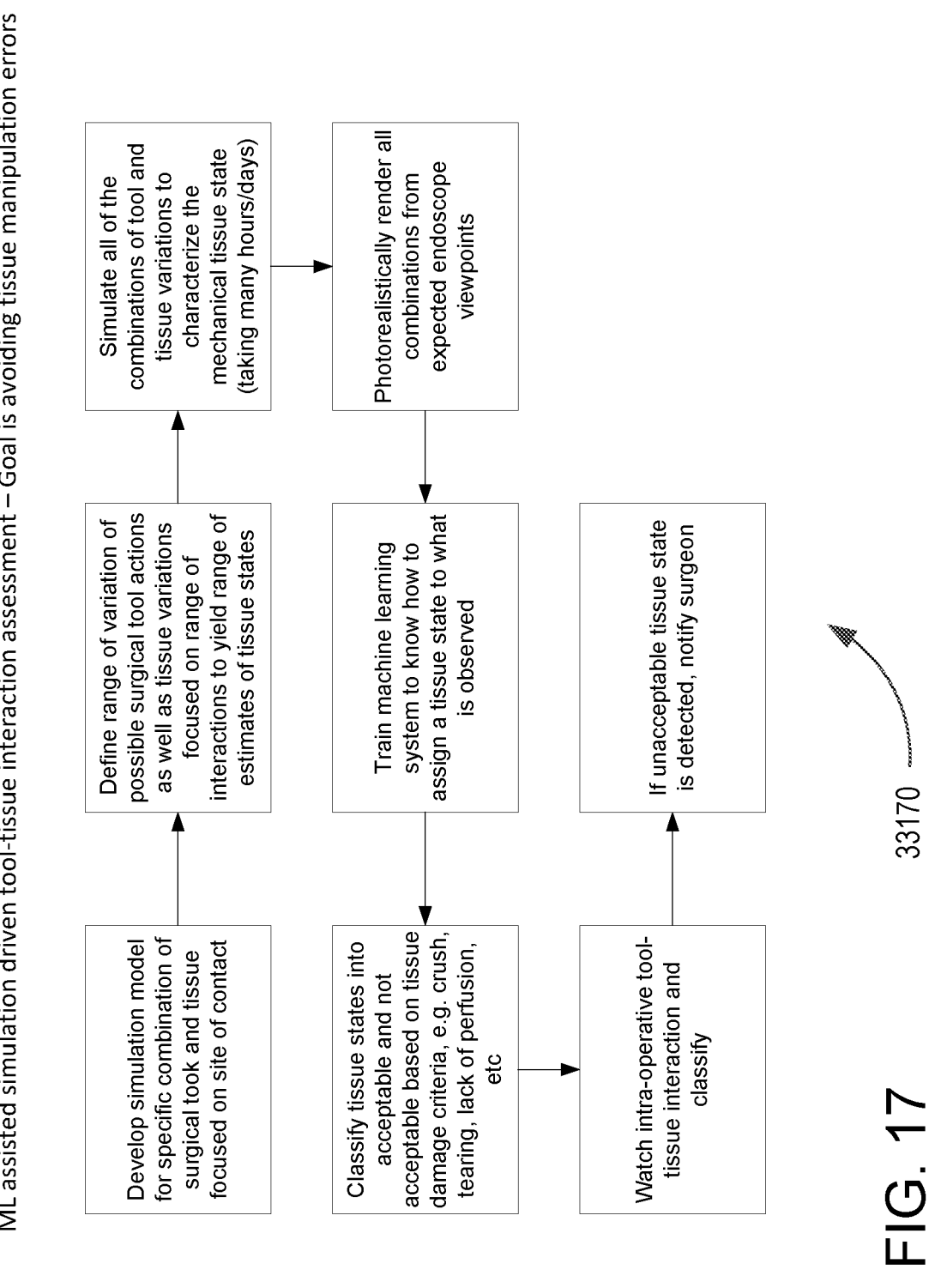

Develop simulation model for specific combination of surgical took and tissue focused on site of contact Define range of variation of possible surgical tool actions as well as tissue variations focused on range of interactions to yield range of estimates of tissue states Simulate all of the combinations of tool and tissue variations to characterize the mechanical tissue state (taking many hours/days)

Photorealistically render all combinations from expected endoscope viewpoints

Train machine learning system to know how to assign a tissue state to what is observed Classify tissue states into acceptable and not acceptable based on tissue damage criteria, e.g. crush, tearing, lack of perfusion, etc Watch intra-operative tool-tissue interaction and classify If unacceptable tissue state is detected, notify surgeon

Determining optimality of patient specific port placement for an overall procedure

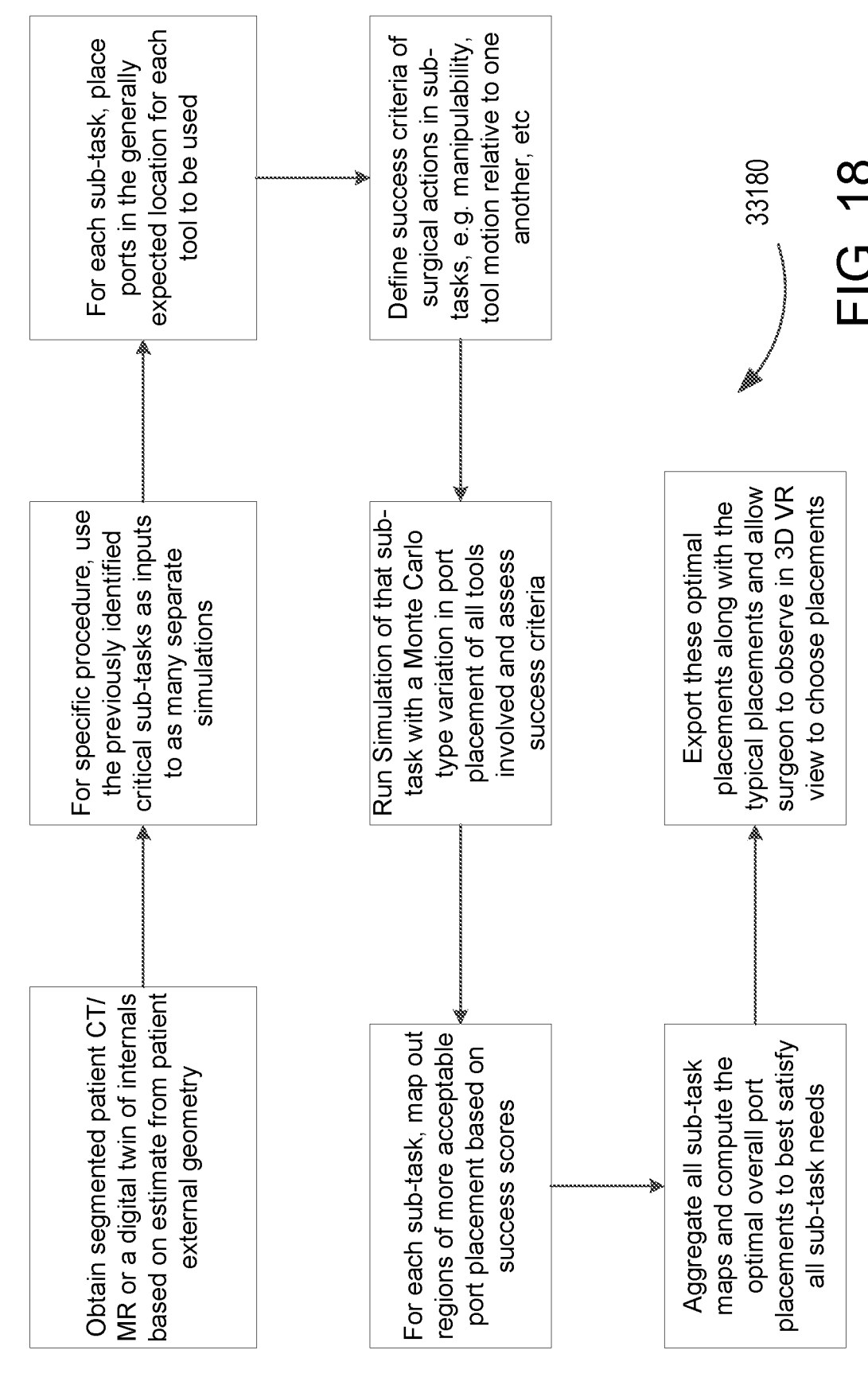

Obtain segmented patient CT/ MR or a digital twin of internals based on estimate from patient external geometry For specific procedure, use the previously identified critical sub-tasks as inputs to as many separate simulations For each sub-task, place ports in the generally expected location for each tool to be used Define success criteria of surgical actions in sub-tasks, e.g. manipulability, tool motion relative to one another, etc Run Simulation of that sub-task with a Monte Carlo type variation in port placement of all tools involved and assess success criteria For each sub-task, map out regions of more acceptable port placement based on success scores Aggregate all sub-task maps and compute the optimal overall port placements to best satisfy all sub-task needs Export these optimal placements along with the typical placements and allow surgeon to observe in 3D VR view to choose placements

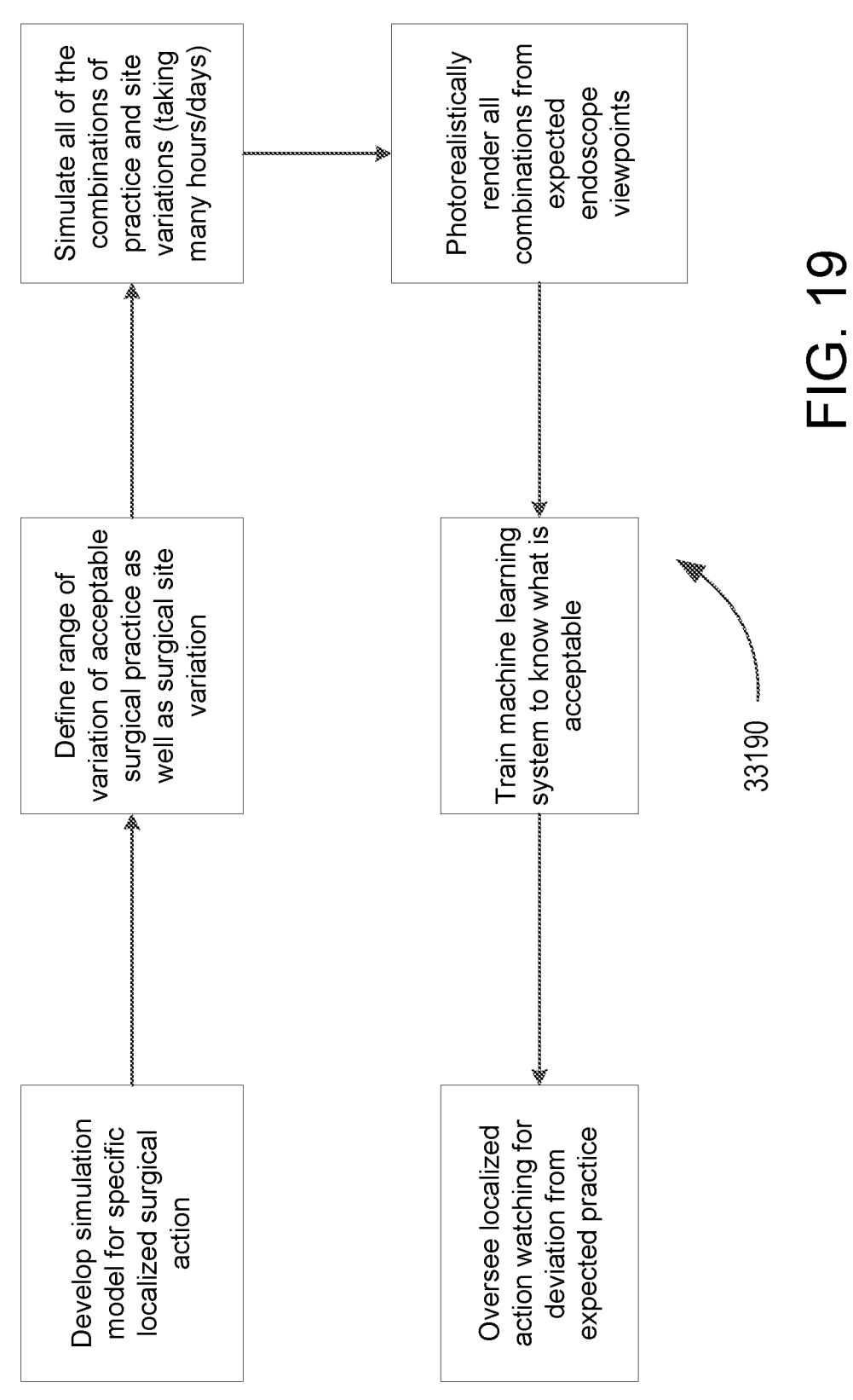

ML assisted simulation driven surgical overseer – Goal is deviation from expected practice Develop simulation model for specific localized surgical action Define range of variation of acceptable surgical practice as well as surgical site variation Simulate all of the combinations of practice and site variations (taking many hours/days)

Photorealistically render all combinations from expected endoscope viewpoints

Train machine learning system to know what is acceptable

Oversee localized action watching for deviation from expected practice

SIMULATION-BASED SURGICAL PROCEDURE PLANNING SYSTEM

CROSS-REFERENCE TO RELATED APPLICATIONS

This application claims the benefit of Provisional U.S. Patent Application No. 63/191,681, May 21, 2021, the disclosure of which is incorporated herein by reference in its entirety.

This application is related to the following, filed contemporaneously, the contents of each of which are incorporated by reference herein:

U.S. patent application Ser. No. 17/332,594, filed May 27, 2021, titled METHODS FOR SURGICAL SIMULATION U.S. patent application Ser. No. 17/332,524, filed May 27, 2021, titled SURGICAL SIMULATION OBJECT RECTIFICATION SYSTEM U.S. patent application Ser. No. 17/332,399, filed May 27, 2021, titled SURGICAL SIMULATION NAVIGATION SYSTEM U.S. patent application Ser. No. 17/332,441, filed May 27, 2021, titled SURGICAL SIMULATION SYSTEM WITH COORDINATED IMAGINING U.S. patent application Ser. No. 17/332,462, filed May 27, 2021, titled SURGICAL SIMULATION SYSTEM WITH SIMULATED SURGICAL EQUIPMENT COORDINATION U.S. patent application Ser. No. 17/332,407, filed May 27, 2021, titled SIMULATION-BASED DIRECTED SURGICAL DEVELOPMENT SYSTEM U.S. patent application Ser. No. 17/332,449, filed May 27, 2021, titled SURGICAL ADVERSE EVENT SIMULATION SYSTEM U.S. patent application Ser. No. 17/332,496, filed May 27, 2021, titled SIMULATION-BASED SURGICAL ANALYSIS SYSTEM U.S. patent application Ser. No. 17/332,480, filed May 27, 2021, titled DYNAMIC ADAPTATION SYSTEM FOR SURGICAL SIMULATION

BACKGROUND

Surgical simulations, such as computer-based, three-dimensional simulations of a surgical environment and/or surgical procedure for example, present an opportunity to advance the surgical arts. Surgical simulations have potential to benefit surgical training, planning, development, and the like. For example, surgical simulations may be used to train surgeons in new procedures and/or to improve the performance of procedures they already know. Surgical simulations may be used as a virtual "dress rehearsal" to help a surgeon prepare for an upcoming procedure. And surgical simulations may be used to experiment with unproven procedures and techniques.

However, surgical simulation platforms are complex systems that face many limitations in capabilities, scope, and applicability. For example, many platforms are technology "silos," specifically programmed and tailored to address a particular learning objective or to simulate the operation of a singular piece of equipment, such as simulating the operation of a surgical robot. Limitations, such as these, may dimmish a platform's effectiveness as a tool to advance the surgical arts. And such limitations may represent significant technological roadblocks to the integration of simulation-based applications into other aspects of the surgical process, such a pre-operative planning, intra-operative support, post-operative analysis, and the like.

Accordingly, innovation in surgical simulation technology, such as technical advancements that address surgical simulation capabilities, scope, and applicability for example, may accelerate further progress in the surgical arts.

SUMMARY

Systems, methods, and instrumentalities are described herein for surgical simulation-based surgical procedure planning. A computing device for generating a surgical procedure plan via surgical simulation may include a processor. The processor may be configured to obtain an indication of a surgical task. The indication of the surgical task is obtained from a surgical procedure planning user interface. The surgical task may be associated with a surgical step of the surgical procedure plan. The processor may be configured to obtain a surgical choice and a corresponding predicted surgical outcome. The processor may be configured to train a machine learning (ML) model using data of a plurality of past surgical procedures. The processor may be configured to generate the surgical choice and the corresponding predicted surgical outcome using the ML model. The surgical choice and the corresponding predicted surgical outcome may be associated with the surgical task. The processor may be configured to generate a visualization of the surgical choice and the corresponding predicted surgical outcome in a simulated environment. The processor may be configured to obtain an indication of the surgical choice being selected. The processor may be configured to store the surgical choice in the surgical procedure plan.

BRIEF DESCRIPTION OF THE DRAWINGS

FIG. 17 illustrates a machine learning (ML)-assisted simulation process for avoiding tissue-manipulation errors.

FIG. 18 illustrates an example process of determining optimality of patient specific port placement for an overall surgical procedure.

FIG. 19 illustrates an example process of detecting deviations from expected practice using ML-assisted simulation.

DETAILED DESCRIPTION

Surgical simulation systems, devices, and methods may include aspects of integration with other medical equipment, data sources, processes, and institutions. Surgical simulation systems, devices, and methods may include aspects of integration with a computer-implemented interactive surgical system and/or with one or more elements of a computer-implemented interactive surgical system, for example.

Figure 1:
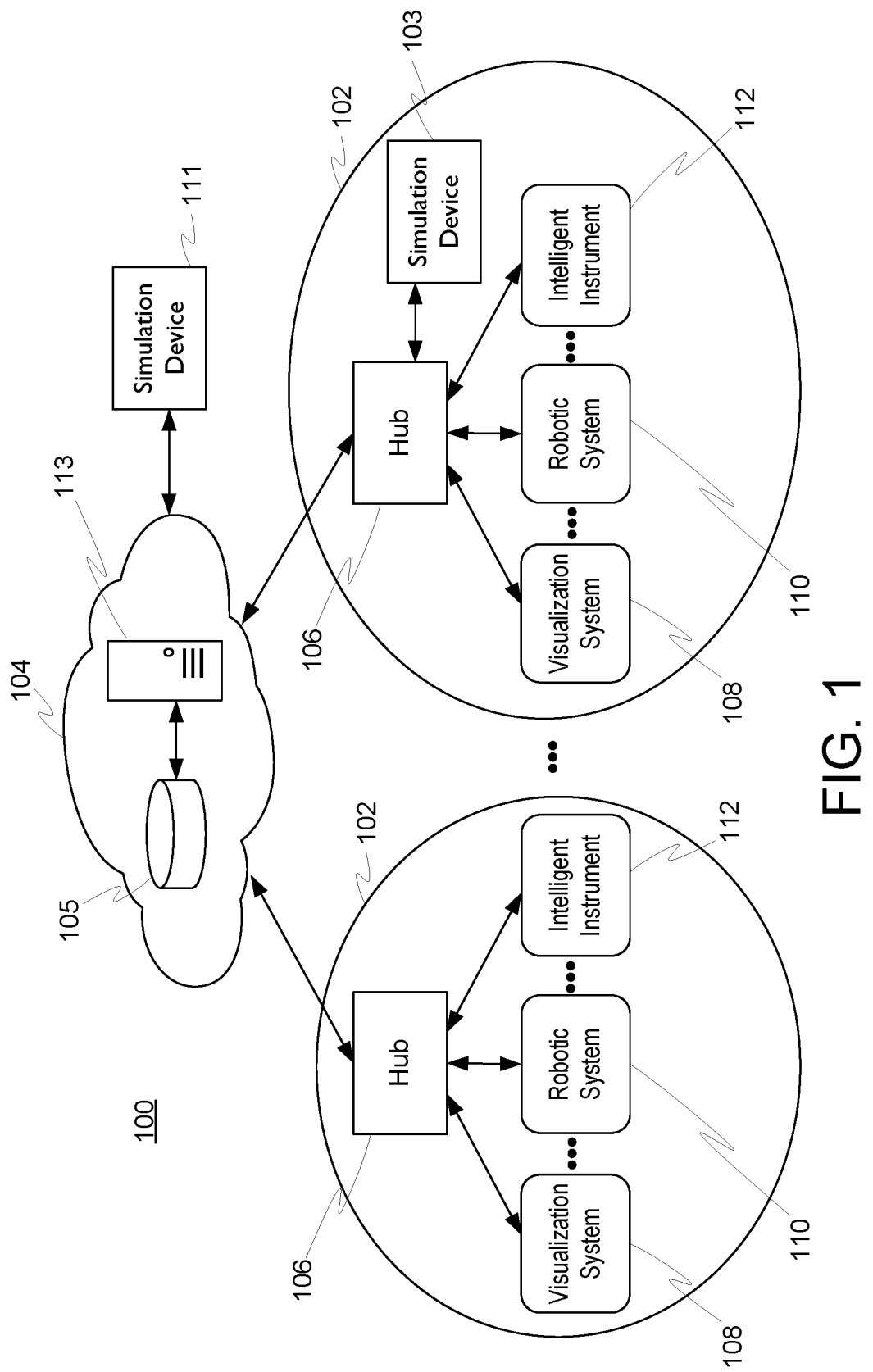
FIG. 1 is a block diagram of a computer-implemented interactive surgical system.

Referring to FIG. 1, a computer-implemented interactive surgical system 100 may include one or more surgical systems 102 and a cloud-based system (e.g., the cloud 104 that may include a remote server 113 coupled to a storage device 105). Each surgical system 102 may include at least one surgical hub 106 in communication with the cloud 104 that may include a remote server 113.

One or more simulation devices 103, 111 may be in communication with and/or integrated as part of the computer-implemented interactive surgical system 100. For example, the simulation device 103 may be an element of the one or more surgical systems 102. For example, the simulation device 103 may be in communication with one or more surgical hubs 106. For example, the simulation device 111 may be in communication with the computer-implemented interactive surgical system 100 via the cloud 104.

In one example, as illustrated in FIG. 1, the surgical system 102 includes a visualization system 108, a robotic system 110, and a handheld intelligent surgical instrument 112, which are configured to communicate with one another and/or the hub 106. In some aspects, a surgical system 102 may include an M number of hubs 106, an N number of visualization systems 108, an O number of robotic systems 110, and a P number of handheld intelligent surgical instruments 112, where M, N, O, and P may be integers greater than or equal to one.

Figure 2:
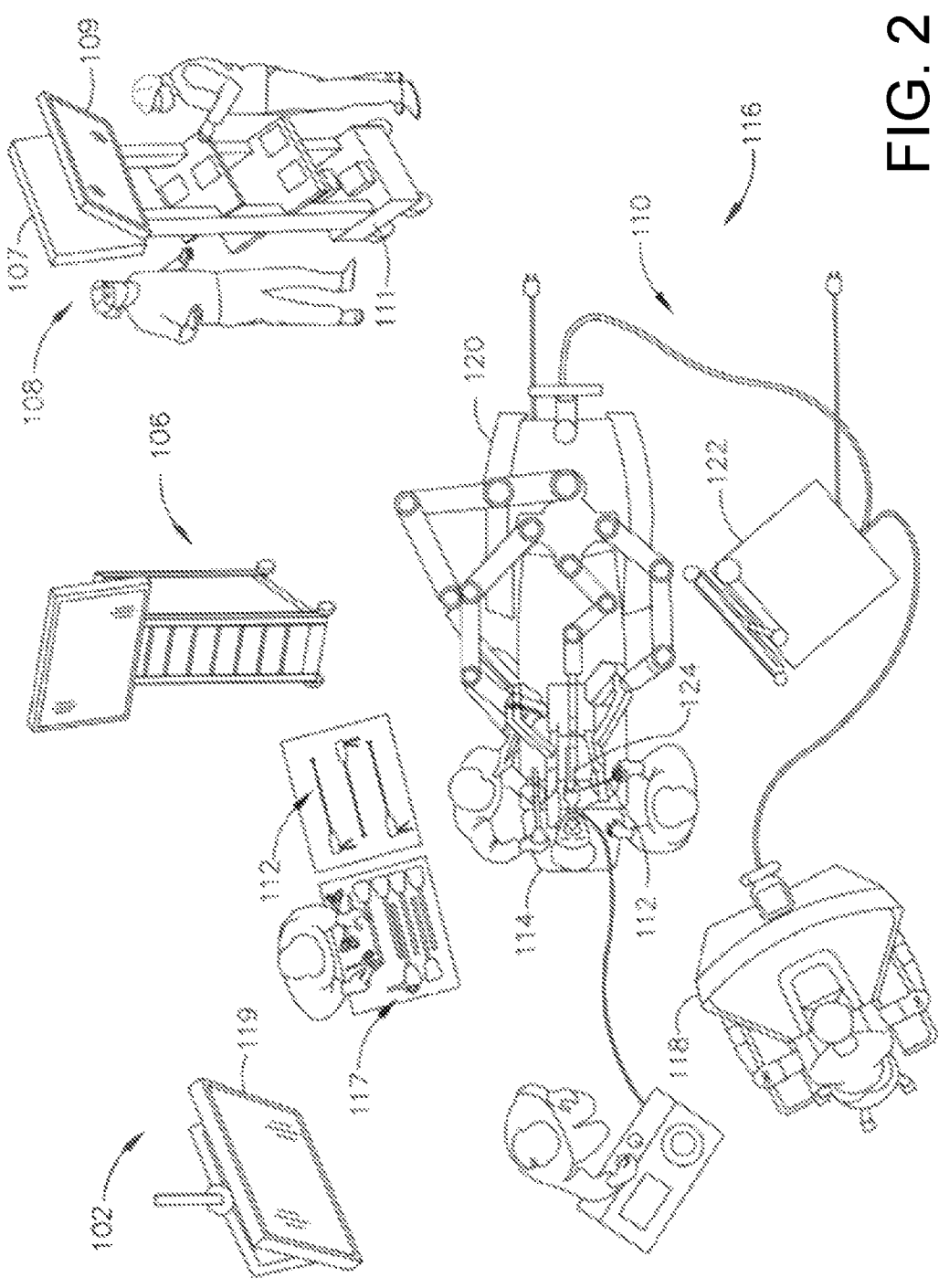
FIG. 2 shows an example surgical system being used to perform a surgical procedure in an operating room.

In various aspects, the visualization system 108 may include one or more imaging sensors, one or more image-processing units, one or more storage arrays, and one or more displays that are strategically arranged with respect to the sterile field, as illustrated in FIG. 2. In one aspect, the visualization system 108 may include an interface for HL7, PACS, and EMR. Various components of the visualization system 108 are described under the heading "Advanced Imaging Acquisition Module" in U.S. Patent Application Publication No. US 2019-0200844 A1 (U.S. patent application Ser. No. 16/209,385), titled METHOD OF HUB COMMUNICATION, PROCESSING, STORAGE AND DISPLAY, filed Dec. 4, 2018, the disclosure of which is herein incorporated by reference in its entirety.

As illustrated in FIG. 2, a primary display 119 is positioned in the sterile field to be visible to an operator at the operating table 114. In addition, a visualization tower 111 is positioned outside the sterile field. The visualization tower 111 may include a first non-sterile display 107 and a second non-sterile display 109, which face away from each other. The visualization system 108, guided by the hub 106, is configured to utilize the displays 107, 109, and 119 to coordinate information flow to operators inside and outside the sterile field. For example, the hub 106 may cause the visualization system 108 to display a snapshot of a surgical site, as recorded by an imaging device 124, on a non-sterile display 107 or 109, while maintaining a live feed of the surgical site on the primary display 119. The snapshot on the non-sterile display 107 or 109 can permit a non-sterile operator to perform a diagnostic step relevant to the surgical procedure, for example.

In one aspect, the hub 106 may also be configured to route a diagnostic input or feedback entered by a non-sterile operator at the visualization tower 111 to the primary display 119 within the sterile field, where it can be viewed by a sterile operator at the operating table. In one example, the input can be in the form of a modification to the snapshot displayed on the non-sterile display 107 or 109, which can be routed to the primary display 119 by the hub 106.

Referring to FIG. 2, a surgical instrument 112 is being used in the surgical procedure as part of the surgical system 102. The hub 106 may also be configured to coordinate information flow to a display of the surgical instrument 112. For example, in U.S. Patent Application Publication No. US 2019-0200844 A1 (U.S. patent application Ser. No. 16/209,385), titled METHOD OF HUB COMMUNICATION, PROCESSING, STORAGE AND DISPLAY, filed Dec. 4, 2018, the disclosure of which is herein incorporated by reference in its entirety. A diagnostic input or feedback entered by a non-sterile operator at the visualization tower 111 can be routed by the hub 106 to the surgical instrument display 115 within the sterile field, where it can be viewed by the operator of the surgical instrument 112. Example surgical instruments that are suitable for use with the surgical system 102 are described under the heading "Surgical Instrument Hardware" and in U.S. Patent Application Publication No. US 2019-0200844 A1 (U.S. patent application Ser. No. 16/209,385), titled METHOD OF HUB COMMUNICATION, PROCESSING, STORAGE AND DISPLAY, filed Dec. 4, 2018, the disclosure of which is herein incorporated by reference in its entirety, for example.

FIG. 2 depicts an example of a surgical system 102 being used to perform a surgical procedure on a patient who is lying down on an operating table 114 in a surgical operating room 116. A robotic system 110 may be used in the surgical procedure as a part of the surgical system 102. The robotic system 110 may include a surgeon's console 118, a patient side cart 120 (surgical robot), and a surgical robotic hub 122. The patient side cart 120 can manipulate at least one removably coupled surgical tool 117 through a minimally invasive incision in the body of the patient while the surgeon views the surgical site through the surgeon's console 118. An image of the surgical site can be obtained by a medical imaging device 124, which can be manipulated by the patient side cart 120 to orient the imaging device 124. The robotic hub 122 can be used to process the images of the surgical site for subsequent display to the surgeon through the surgeon's console 118.

Other types of robotic systems can be readily adapted for use with the surgical system 102. Various examples of robotic systems and surgical tools that are suitable for use with the present disclosure are described in U.S. Patent Application Publication No. US 2019-0201137 A1 (U.S. patent application Ser. No. 16/209,407), titled METHOD OF ROBOTIC HUB COMMUNICATION, DETECTION, AND CONTROL, filed Dec. 4, 2018, the disclosure of which is herein incorporated by reference in its entirety.

Various examples of cloud-based analytics that are performed by the cloud 104, and are suitable for use with the present disclosure, are described in U.S. Patent Application Publication No. US 2019-0206569 A1 (U.S. patent application Ser. No. 16/209,403), titled METHOD OF CLOUD BASED DATA ANALYTICS FOR USE WITH THE HUB, filed Dec. 4, 2018, the disclosure of which is herein incorporated by reference in its entirety.

In various aspects, the imaging device 124 may include at least one image sensor and one or more optical components. Suitable image sensors may include, but are not limited to, Charge-Coupled Device (CCD) sensors and Complementary Metal-Oxide Semiconductor (CMOS) sensors.

The optical components of the imaging device 124 may include one or more illumination sources and/or one or more lenses. The one or more illumination sources may be directed to illuminate portions of the surgical field. The one or more image sensors may receive light reflected or refracted from the surgical field, including light reflected or refracted from tissue and/or surgical instruments.

The one or more illumination sources may be configured to radiate electromagnetic energy in the visible spectrum as well as the invisible spectrum. The visible spectrum, sometimes referred to as the optical spectrum or luminous spectrum, is that portion of the electromagnetic spectrum that is visible to (i.e., can be detected by) the human eye and may be referred to as visible light or simply light. A typical human eye will respond to wavelengths in air that are from about 380 nm to about 750 nm.

The invisible spectrum (e.g., the non-luminous spectrum) is that portion of the electromagnetic spectrum that lies below and above the visible spectrum (i.e., wavelengths below about 380 nm and above about 750 nm). The invisible spectrum is not detectable by the human eye. Wavelengths greater than about 750 nm are longer than the red visible spectrum, and they become invisible infrared (IR), microwave, and radio electromagnetic radiation. Wavelengths less than about 380 nm are shorter than the violet spectrum, and they become invisible ultraviolet, x-ray, and gamma ray electromagnetic radiation.

In various aspects, the imaging device 124 is configured for use in a minimally invasive procedure. Examples of imaging devices suitable for use with the present disclosure include, but not limited to, an arthroscope, angioscope, bronchoscope, choledochoscope, colonoscope, cytoscope, duodenoscope, enteroscope, esophagogastro-duodenoscope (gastroscope), endoscope, laryngoscope, nasopharyngo-neproscope, sigmoidoscope, thoracoscope, and uretero-scope.

The imaging device may employ multi-spectrum monitoring to discriminate topography and underlying structures. A multi-spectral image is one that captures image data within specific wavelength ranges across the electromagnetic spectrum. The wavelengths may be separated by filters or by the use of instruments that are sensitive to particular wavelengths, including light from frequencies beyond the visible light range, e.g., IR and ultraviolet. Spectral imaging can allow extraction of additional information the human eye fails to capture with its receptors for red, green, and blue. The use of multi-spectral imaging is described in greater detail under the heading "Advanced Imaging Acquisition Module" in .S. Patent Application Publication No. US 2019-0200844 A1 (U.S. patent application Ser. No. 16/209, 385), titled METHOD OF HUB COMMUNICATION, PROCESSING, STORAGE AND DISPLAY, filed Dec. 4, 2018, the disclosure of which is herein incorporated by reference in its entirety. Multi-spectrum monitoring can be a useful tool in relocating a surgical field after a surgical task is completed to perform one or more of the previously described tests on the treated tissue. It is axiomatic that strict sterilization of the operating room and surgical equipment is required during any surgery. The strict hygiene and sterilization conditions required in a "surgical theater," i.e., an operating or treatment room, necessitate the highest possible sterility of all medical devices and equipment. Part of that sterilization process is the need to sterilize anything that comes in contact with the patient or penetrates the sterile field, including the imaging device 124 and its attachments and components. It will be appreciated that the sterile field may be considered a specified area, such as within a tray or on a sterile towel, that is considered free of microorganisms, or the sterile field may be considered an area, immediately around a patient, who has been prepared for a surgical procedure. The sterile field may include the scrubbed team members, who are properly attired, and all furniture and fixtures in the area.

Figure 3:
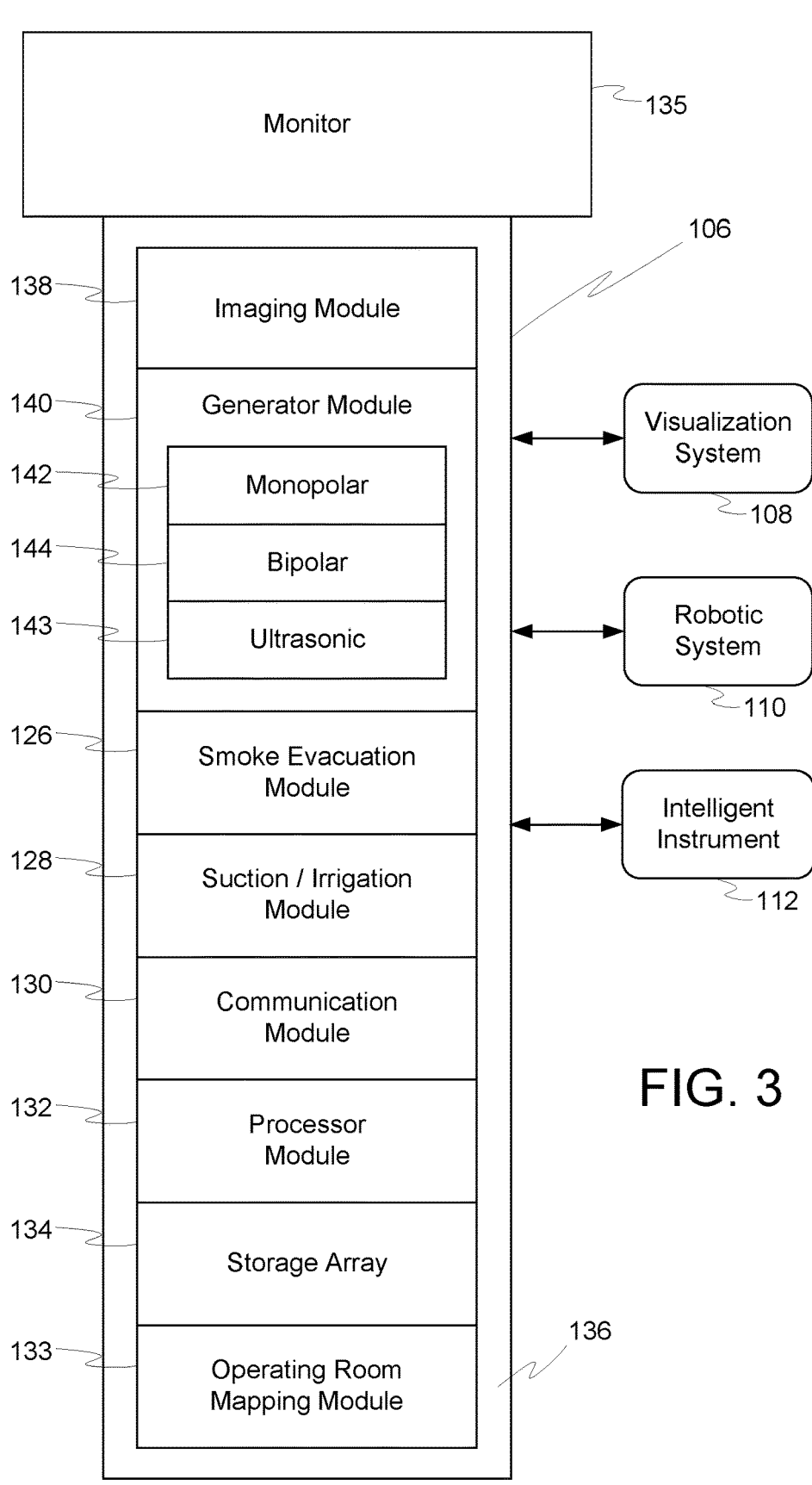
FIG. 3 shows an example surgical hub paired with a visualization system, a robotic system, and an intelligent instrument, in accordance with at least one aspect of the present disclosure.

Referring now to FIG. 3, a hub 106 is depicted in communication with a visualization system 108, a robotic system 110, and a handheld intelligent surgical instrument 112. The hub 106 includes a hub display 135, an imaging module 138, a generator module 140, a communication module 130, a processor module 132, a storage array 134, and an operating-room mapping module 133. In certain aspects, as illustrated in FIG. 3, the hub 106 further includes a smoke evacuation module 126 and/or a suction/irrigation module 128. During a surgical procedure, energy application to tissue, for sealing and/or cutting, is generally associated with smoke evacuation, suction of excess fluid, and/or irrigation of the tissue. Fluid, power, and/or data lines from different sources are often entangled during the surgical procedure. Valuable time can be lost addressing this issue during a surgical procedure. Detangling the lines may necessitate disconnecting the lines from their respective modules, which may require resetting the modules. The hub modular enclosure 136 offers a unified environment for managing the power, data, and fluid lines, which reduces the frequency of entanglement between such lines. Aspects of the present disclosure present a surgical hub for use in a surgical procedure that involves energy application to tissue at a surgical site. The surgical hub includes a hub enclosure and a combo generator module slidably receivable in a docking station of the hub enclosure. The docking station includes data and power contacts. The combo generator module includes two or more of an ultrasonic energy generator component, a bipolar RF energy generator component, and a monopolar RF energy generator component that are housed in a single unit. In one aspect, the combo generator module also includes a smoke evacuation component, at least one energy delivery cable for connecting the combo generator module to a surgical instrument, at least one smoke evacuation component configured to evacuate smoke, fluid, and/or particulates generated by the application of therapeutic energy to the tissue, and a fluid line extending from the remote surgical site to the smoke evacuation component. In one aspect, the fluid line is a first fluid line and a second fluid line extends from the remote surgical site to a suction and irrigation module slidably received in the hub enclosure. In one aspect, the hub enclosure comprises a fluid interface. Certain surgical procedures may require the application of more than one energy type to the tissue. One energy type may be more beneficial for cutting the tissue, while another different energy type may be more beneficial for sealing the tissue. For example, a bipolar generator can be used to seal the tissue while an ultrasonic generator can be used to cut the sealed tissue. Aspects of the present disclosure present a solution where a hub modular enclosure 136 is configured to accommodate different generators, and facilitate an interactive communication therebetween. One of the advantages of the hub modular enclosure 136 is enabling the quick removal and/or replacement of various modules. Aspects of the present disclosure present a modular surgical enclosure for use in a surgical procedure that involves energy application to tissue. The modular surgical enclosure includes a first energy-generator module, configured to generate a first energy for application to the tissue, and a first docking station comprising a first docking port that includes first data and power contacts, wherein the first energy-generator module is slidably movable into an electrical engagement with the power and data contacts and wherein the first energy-generator module is slidably movable out of the electrical engagement with the first power and data contacts. Further to the above, the modular surgical enclosure also includes a second energy-generator module con-figured to generate a second energy, different than the first energy, for application to the tissue, and a second docking station comprising a second docking port that includes second data and power contacts, wherein the second energy-generator module is slidably movable into an electrical engagement with the power and data contacts, and wherein the second energy-generator module is slidably movable out of the electrical engagement with the second power and data contacts. In addition, the modular surgical enclosure also includes a communication bus between the first docking port and the second docking port, configured to facilitate com-munication between the first energy-generator module and the second energy-generator module. Referring to FIG. 3, aspects of the present disclosure are presented for a hub modular enclosure 136 that allows the modular integration of a generator module 140, a smoke evacuation module 126, and a suction/irrigation module 128. The hub modular enclosure 136 further facilitates interactive com-munication between the modules 140, 126, 128. The gen-erator module 140 can be a generator module with integrated monopolar, bipolar, and ultrasonic components supported in a single housing unit slidably insertable into the hub modu-lar enclosure 136. The generator module 140 can be con-figured to connect to a monopolar device 142, a bipolar device 144, and an ultrasonic device 146. Alternatively, the generator module 140 may comprise a series of monopolar, bipolar, and/or ultrasonic generator modules that interact through the hub modular enclosure 136. The hub modular enclosure 136 can be configured to facilitate the insertion of multiple generators and interactive communication between the generators docked into the hub modular enclosure 136 so that the generators would act as a single generator.

Figure 4:
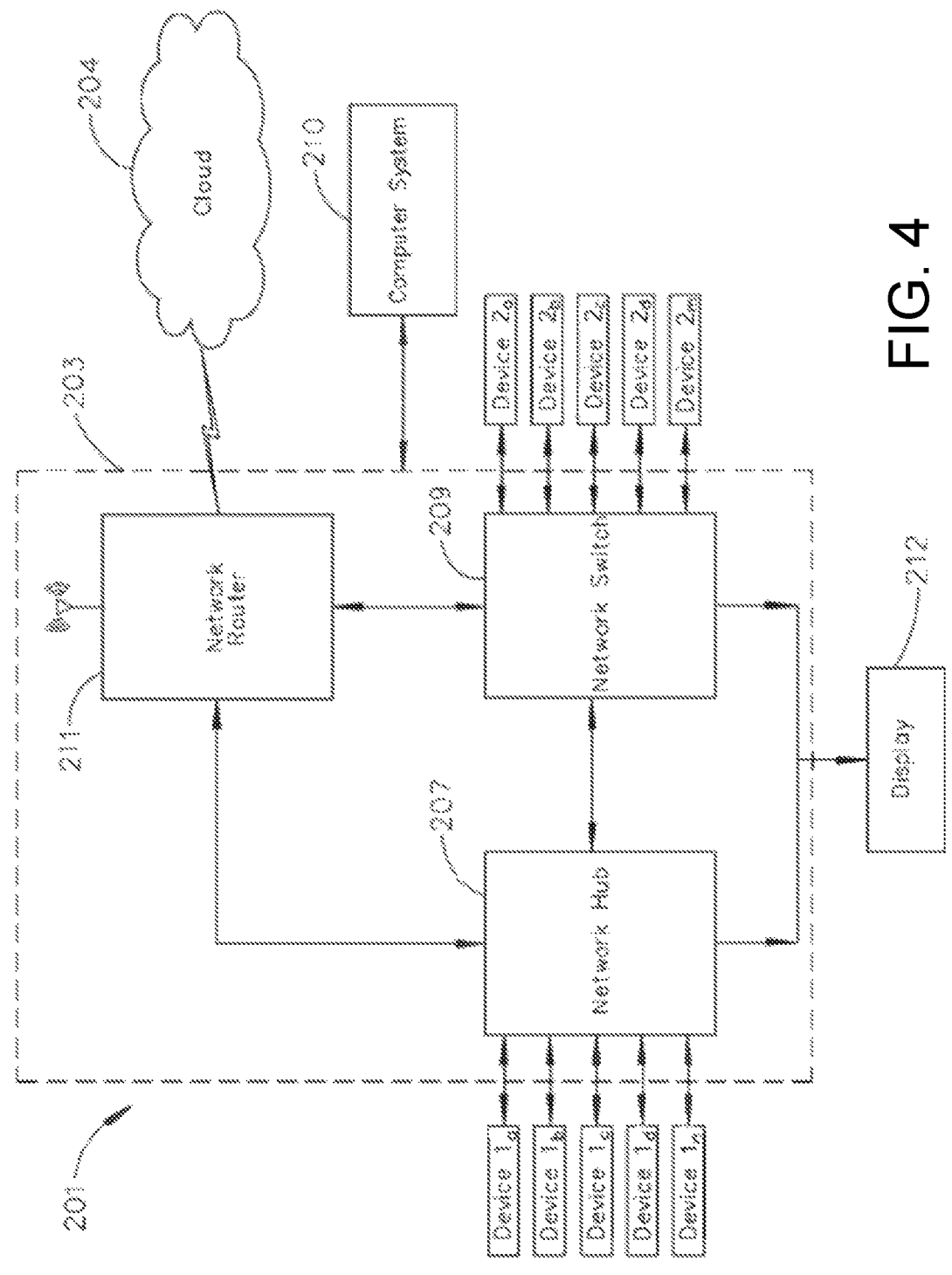
FIG. 4 illustrates a surgical data network having a communication hub configured to connect modular devices located in one or more operating theaters of a healthcare facility, or any room in a healthcare facility specially equipped for surgical operations, to the cloud, in accordance with at least one aspect of the present disclosure.

FIG. 4 illustrates a surgical data network 201 comprising a modular communication hub 203 configured to connect modular devices located in one or more operating theaters of a healthcare facility, or any room in a healthcare facility specially equipped for surgical operations, to a cloud-based system (e.g., the cloud 204 that may include a remote server 213 coupled to a storage device 205). In one aspect, the modular communication hub 203 comprises a network hub 207 and/or a network switch 209 in communication with a network router. The modular communication hub 203 also can be coupled to a local computer system 210 to provide local computer processing and data manipulation. The sur-gical data network 201 may be configured as passive, intelligent, or switching. A passive surgical data network serves as a conduit for the data, enabling it to go from one device (or segment) to another and to the cloud computing resources. An intelligent surgical data network includes additional features to enable the traffic passing through the surgical data network to be monitored and to configure each port in the network hub 207 or network switch 209. An intelligent surgical data network may be referred to as a manageable hub or switch. A switching hub reads the destination address of each packet and then forwards the packet to the correct port.

Modular devices 1a-1n located in the operating theater may be coupled to the modular communication hub 203. The network hub 207 and/or the network switch 209 may be coupled to a network router 211 to connect the devices 1a-1n to the cloud 204 or the local computer system 210. Data associated with the devices 1a-1n may be transferred to cloud-based computers via the router for remote data pro-cessing and manipulation. Data associated with the devices 1a-1n may also be transferred to the local computer system 210 for local data processing and manipulation. Modular devices 2a-2m located in the same operating theater also may be coupled to a network switch 209. The network switch 209 may be coupled to the network hub 207 and/or the network router 211 to connect to the devices 2a-2m to the cloud 204. Data associated with the devices 2a-2n may be transferred to the cloud 204 via the network router 211 for data processing and manipulation. Data associated with the devices 2a-2m may also be transferred to the local computer system 210 for local data processing and manipulation.

It will be appreciated that the surgical data network 201 may be expanded by interconnecting multiple network hubs 207 and/or multiple network switches 209 with multiple network routers 211. The modular communication hub 203 may be contained in a modular control tower configured to receive multiple devices 1a-1n/2a-2m. The local computer system 210 also may be contained in a modular control tower. The modular communication hub 203 is connected to a display 212 to display images obtained by some of the devices 1a-1n/2a-2m, for example during surgical proce-dures. In various aspects, the devices 1a-1n/2a-2m may include, for example, various modules such as an imaging module 138 coupled to an endoscope, a generator module 140 coupled to an energy-based surgical device, a smoke evacuation module 126, a suction/irrigation module 128, a communication module 130, a processor module 132, a storage array 134, a surgical device coupled to a display, and/or a non-contact sensor module, among other modular devices that may be connected to the modular communica-tion hub 203 of the surgical data network 201.

In one aspect, the surgical data network 201 may com-prise a combination of network hub(s), network switch(es), and network router(s) connecting the devices 1a-1n/2a-2m to the cloud. Any one of or all of the devices 1a-1n/2a-2m coupled to the network hub or network switch may collect data in real time and transfer the data to cloud computers for data processing and manipulation. It will be appreciated that cloud computing relies on sharing computing resources rather than having local servers or personal devices to handle software applications. The word "cloud" may be used as a metaphor for "the Internet," although the term is not limited as such. Accordingly, the term "cloud computing" may be used herein to refer to "a type of Internet-based computing," where different services—such as servers, storage, and applications—are delivered to the modular communication hub 203 and/or computer system 210 located in the surgical theater (e.g., a fixed, mobile, temporary, or field operating room or space) and to devices connected to the modular communication hub 203 and/or computer system 210 through the Internet. The cloud infrastructure may be maintained by a cloud service provider. In this context, the cloud service provider may be the entity that coordinates the usage and control of the devices 1a-1n/2a-2m located in one or more operating theaters. The cloud computing services can perform a large number of calculations based on the data gathered by smart surgical instruments, robots, and other computerized devices located in the operating theater. The hub hardware enables multiple devices or connections to be connected to a computer that communicates with the cloud computing resources and storage.

Applying cloud computer data processing techniques on the data collected by the devices 1a-1n/2a-2m, the surgical data network can provide improved surgical outcomes, reduced costs, and improved patient satisfaction. At least some of the devices 1a-1n/2a-2m may be employed to view tissue states to assess leaks or perfusion of sealed tissue after a tissue sealing and cutting procedure. At least some of the devices 1a-1n/2a-2m may be employed to identify pathology, such as the effects of diseases, using the cloud-based computing to examine data including images of samples of body tissue for diagnostic purposes. This may include localization and margin confirmation of tissue and phenotypes. At least some of the devices 1a-1n/2a-2m may be employed to identify anatomical structures of the body using a variety of sensors integrated with imaging devices and techniques such as overlaying images captured by multiple imaging devices. The data gathered by the devices 1a-1n/2a-2m, including image data, may be transferred to the cloud 204 or the local computer system 210 or both for data processing and manipulation including image processing and manipulation. The data may be analyzed to improve surgical procedure outcomes by determining if further treatment, such as the application of endoscopic intervention, emerging technologies, a targeted radiation, targeted intervention, and precise robotics to tissue-specific sites and conditions, may be pursued. Such data analysis may further employ outcome analytics processing, and using standardized approaches may provide beneficial feedback to either confirm surgical treatments and the behavior of the surgeon or suggest modifications to surgical treatments and the behavior of the surgeon.

The operating theater devices 1a-1n may be connected to the modular communication hub 203 over a wired channel or a wireless channel depending on the configuration of the devices 1a-1n to a network hub. The network hub 207 may be implemented, in one aspect, as a local network broadcast device that works on the physical layer of the Open System Interconnection (OSI) model. The network hub may provide connectivity to the devices 1a-1n located in the same operating theater network. The network hub 207 may collect data in the form of packets and sends them to the router in half duplex mode. The network hub 207 may not store any media access control/Internet Protocol (MAC/IP) to transfer the device data. Only one of the devices 1a-1n can send data at a time through the network hub 207. The network hub 207 may not have routing tables or intelligence regarding where to send information and broadcasts all network data across each connection and to a remote server 213 (FIG. 4) over the cloud 204. The network hub 207 can detect basic network errors such as collisions, but having all information broadcast to multiple ports can be a security risk and cause bottlenecks.

The operating theater devices 2a-2m may be connected to a network switch 209 over a wired channel or a wireless channel. The network switch 209 works in the data link layer of the OSI model. The network switch 209 may be a multicast device for connecting the devices 2a-2m located in the same operating theater to the network. The network switch 209 may send data in the form of frames to the network router 211 and works in full duplex mode. Multiple devices 2a-2m can send data at the same time through the network switch 209. The network switch 209 stores and uses MAC addresses of the devices 2a-2m to transfer data.

The network hub 207 and/or the network switch 209 may be coupled to the network router 211 for connection to the cloud 204. The network router 211 works in the network layer of the OSI model. The network router 211 creates a route for transmitting data packets received from the network hub 207 and/or network switch 211 to cloud-based computer resources for further processing and manipulation of the data collected by any one of or all the devices 1a-1n/2a-2m. The network router 211 may be employed to connect two or more different networks located in different locations, such as, for example, different operating theaters of the same healthcare facility or different networks located in different operating theaters of different healthcare facilities. The network router 211 may send data in the form of packets to the cloud 204 and works in full duplex mode. Multiple devices can send data at the same time. The network router 211 uses IP addresses to transfer data.

In an example, the network hub 207 may be implemented as a USB hub, which allows multiple USB devices to be connected to a host computer. The USB hub may expand a single USB port into several tiers so that there are more ports available to connect devices to the host system computer. The network hub 207 may include wired or wireless capabilities to receive information over a wired channel or a wireless channel. In one aspect, a wireless USB short-range, high-bandwidth wireless radio communication protocol may be employed for communication between the devices 1a-1n and devices 2a-2m located in the operating theater.

In examples, the operating theater devices 1a-1n/2a-2m may communicate to the modular communication hub 203 via Bluetooth wireless technology standard for exchanging data over short distances (using short-wavelength UHF radio waves in the ISM band from 2.4 to 2.485 GHz) from fixed and mobile devices and building personal area networks (PANs). The operating theater devices 1a-1n/2a-2m may communicate to the modular communication hub 203 via a number of wireless or wired communication standards or protocols, including but not limited to Wi-Fi (IEEE 802.11 family), WiMAX (IEEE 802.16 family), IEEE 802.20, new radio (NR), long-term evolution (LTE), and Ev-DO, HSPA+, HSDPA+, HSUPA+, EDGE, GSM, GPRS, CDMA, TDMA, DECT, and Ethernet derivatives thereof, as well as any other wireless and wired protocols that are designated as 3G, 4G, 5G, and beyond. The computing module may include a plurality of communication modules. For instance, a first communication module may be dedicated to shorter-range wireless communications such as Wi-Fi and Bluetooth, and a second communication module may be dedicated to longer-range wireless communications such as GPS, EDGE, GPRS, CDMA, WiMAX, LTE, Ev-DO, and others.

The modular communication hub 203 may serve as a central connection for one or all of the operating theater devices 1a-1n/2a-2m and may handle a data type known as frames. Frames may carry the data generated by the devices 1a-1n/2a-2m. When a frame is received by the modular communication hub 203, it is amplified and transmitted to the network router 211, which transfers the data to the cloud computing resources by using a number of wireless or wired communication standards or protocols, as described herein.

The modular communication hub 203 can be used as a standalone device or be connected to compatible network hubs and network switches to form a larger network. The modular communication hub 203 can be generally easy to install, configure, and maintain, making it a good option for networking the operating theater devices 1a-1n/2a-2m.

Figure 5:
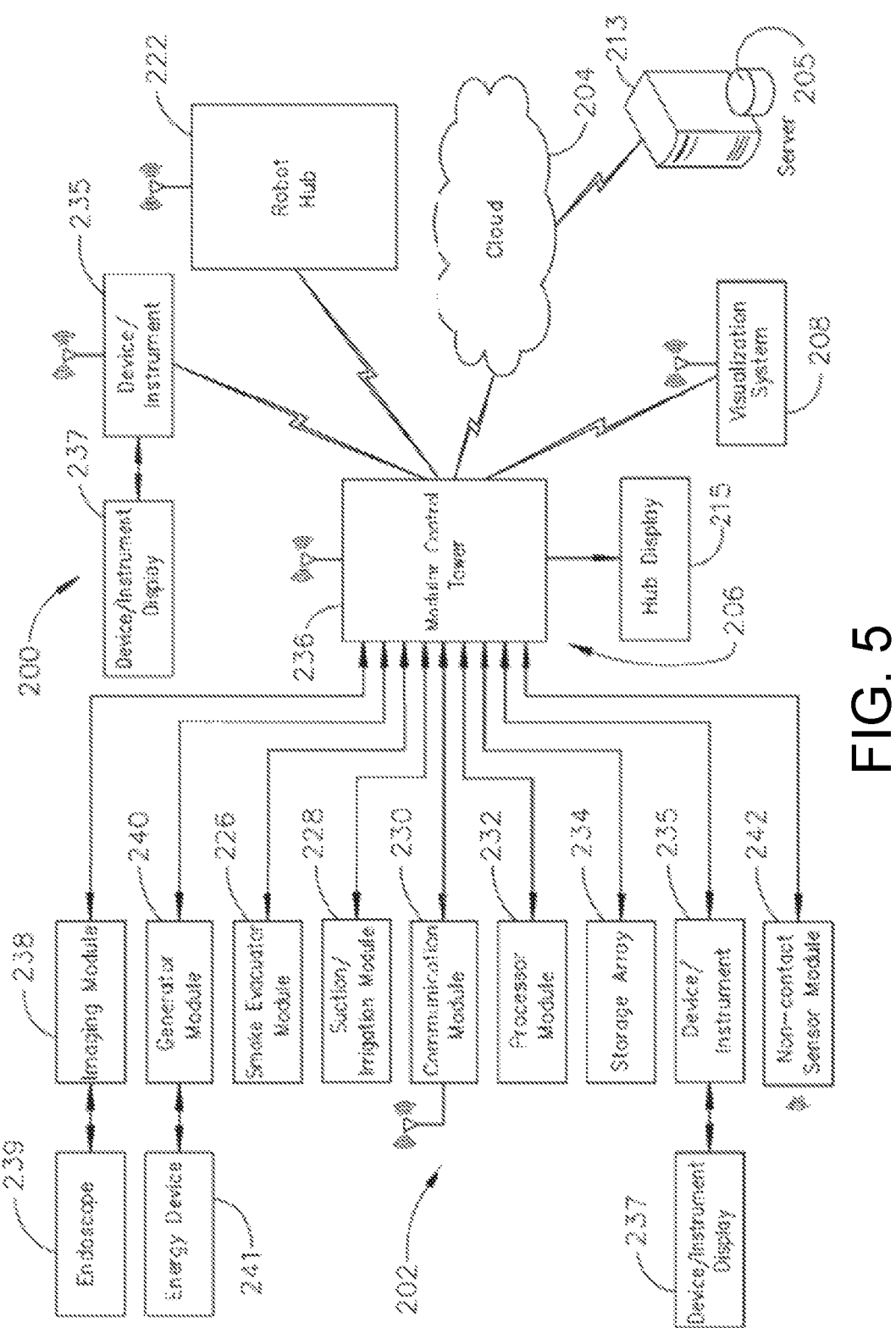
FIG. 5 illustrates an example computer-implemented interactive surgical system.
Figure 6:
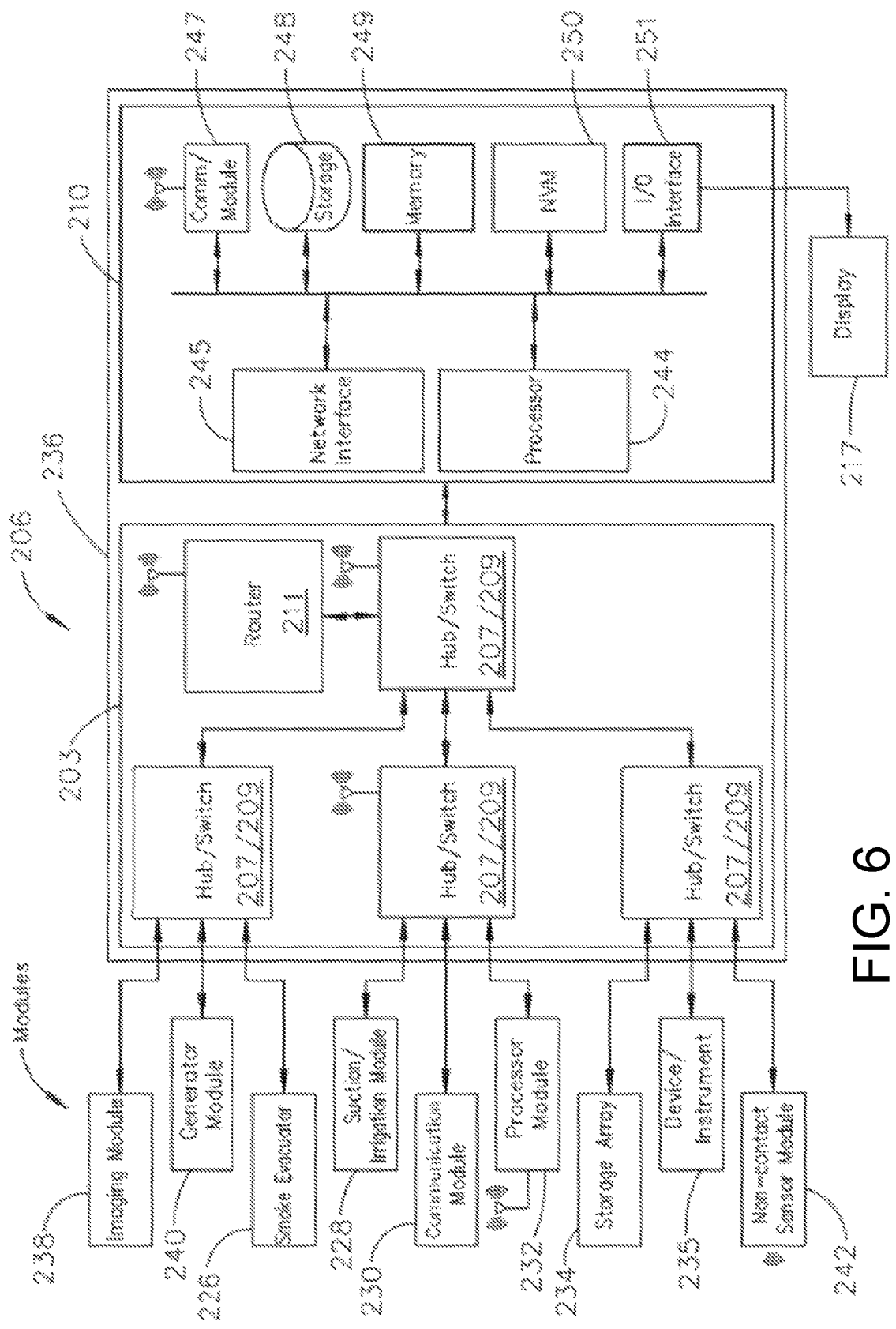
FIG. 6 illustrates an example surgical hub comprising a plurality of modules coupled to the modular control tower.

FIG. 5 illustrates a computer-implemented interactive surgical system 200. The computer-implemented interactive surgical system 200 is similar in many respects to the computer-implemented interactive surgical system 100. For example, the computer-implemented interactive surgical system 200 includes one or more surgical systems 202, which are similar in many respects to the surgical systems 102. Each surgical system 202 includes at least one surgical hub 206 in communication with a cloud 204 that may include a remote server 213. In one aspect, the computer-implemented interactive surgical system 200 comprises a modular control tower 236 connected to multiple operating theater devices such as, for example, intelligent surgical instruments, robots, and other computerized devices located in the operating theater. As shown in FIG. 6, the modular control tower 236 comprises a modular communication hub 203 coupled to a computer system 210.

As illustrated in the example of FIG. 5, the modular control tower 236 may be coupled to an imaging module 238 that may be coupled to an endoscope 239, a generator module 240 that may be coupled to an energy device 241, a smoke evacuator module 226, a suction/irrigation module 228, a communication module 230, a processor module 232, a storage array 234, a smart device/instrument 235 optionally coupled to a display 237, and a non-contact sensor module 242. The operating theater devices may be coupled to cloud computing resources and data storage via the modular control tower 236. A robot hub 222 also may be connected to the modular control tower 236 and to the cloud computing resources. The devices/instruments 235, visualization systems 208, among others, may be coupled to the modular control tower 236 via wired or wireless communication standards or protocols, as described herein. The modular control tower 236 may be coupled to a hub display 215 (e.g., monitor, screen) to display and overlay images received from the imaging module, device/instrument display, and/or other visualization systems 208. The hub display also may display data received from devices connected to the modular control tower in conjunction with images and overlaid images.

FIG. 6 illustrates a surgical hub 206 comprising a plurality of modules coupled to the modular control tower 236. The modular control tower 236 may comprise a modular communication hub 203, e.g., a network connectivity device, and a computer system 210 to provide local processing, visualization, and imaging, for example. As shown in FIG. 6, the modular communication hub 203 may be connected in a tiered configuration to expand the number of modules (e.g., devices) that may be connected to the modular communication hub 203 and transfer data associated with the modules to the computer system 210, cloud computing resources, or both. As shown in FIG. 6, each of the network hubs/switches in the modular communication hub 203 may include three downstream ports and one upstream port. The upstream network hub/switch may be connected to a processor to provide a communication connection to the cloud computing resources and a local display 217. Communication to the cloud 204 may be made either through a wired or a wireless communication channel.

The surgical hub 206 may employ a non-contact sensor module 242 to measure the dimensions of the operating theater and generate a map of the surgical theater using either ultrasonic or laser-type non-contact measurement devices. An ultrasound-based non-contact sensor module may scan the operating theater by transmitting a burst of ultrasound and receiving the echo when it bounces off the perimeter walls of an operating theater as described under the heading "Surgical Hub Spatial Awareness Within an Operating Room" in S. Patent Application Publication No. US 2019-0200844 A1 (U.S. patent application Ser. No. 16/209,385), titled METHOD OF HUB COMMUNICATION, PROCESSING, STORAGE AND DISPLAY, filed Dec. 4, 2018, which is herein incorporated by reference in its entirety, in which the sensor module is configured to determine the size of the operating theater and to adjust Bluetooth-pairing distance limits. A laser-based non-contact sensor module may scan the operating theater by transmitting laser light pulses, receiving laser light pulses that bounce off the perimeter walls of the operating theater, and comparing the phase of the transmitted pulse to the received pulse to determine the size of the operating theater and to adjust Bluetooth pairing distance limits, for example.

The computer system 210 may comprise a processor 244 and a network interface 245. The processor 244 can be coupled to a communication module 247, storage 248, memory 249, non-volatile memory 250, and input/output interface 251 via a system bus. The system bus can be any of several types of bus structure(s) including the memory bus or memory controller, a peripheral bus or external bus, and/or a local bus using any variety of available bus architectures including, but not limited to, 9-bit bus, Industrial Standard Architecture (ISA), Micro-Charmel Architecture (VISA), Extended ISA (EISA), Intelligent Drive Electronics (IDE), VESA Local Bus (VLB), Peripheral Component Interconnect (PCI), USB, Advanced Graphics Port (AGP), Personal Computer Memory Card International Association bus (PCMCIA), Small Computer Systems Interface (SCSI), or any other proprietary bus.

The processor 244 may be any single-core or multicore processor such as those known under the trade name ARM Cortex by Texas Instruments. In one aspect, the processor may be an LM4F230H5QR ARM Cortex-M4F Processor Core, available from Texas Instruments, for example, comprising an on-chip memory of 256 KB single-cycle flash memory, or other non-volatile memory, up to 40 MHz, a prefetch buffer to improve performance above 40 MHz, a 32 KB single-cycle serial random access memory (SRAM), an internal read-only memory (ROM) loaded with StellarisWare® software, a 2 KB electrically erasable programmable read-only memory (EEPROM), and/or one or more pulse width modulation (PWM) modules, one or more quadrature encoder inputs (QEI) analogs, one or more 12-bit analog-to-digital converters (ADCs) with 12 analog input channels, details of which are available for the product datasheet.

In one aspect, the processor 244 may comprise a safety controller comprising two controller-based families such as TMS570 and RM4x, known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

The system memory may include volatile memory and non-volatile memory. The basic input/output system (BIOS), containing the basic routines to transfer information between elements within the computer system, such as during start-up, is stored in non-volatile memory. For example, the non-volatile memory can include ROM, programmable ROM (PROM), electrically programmable ROM (EPROM), EEPROM, or flash memory. Volatile memory includes random-access memory (RAM), which acts as external cache memory. Moreover, RAM is available in many forms such as SRAM, dynamic RAM (DRAM), synchronous DRAM (SDRAM), double data rate SDRAM (DDR SDRAM), enhanced SDRAM (ESDRAM), Synchlink DRAM (SL-DRAM), and direct Rambus RAM (DRRAM).

The computer system 210 also may include removable/ non-removable, volatile/non-volatile computer storage media, such as for example disk storage. The disk storage can include, but is not limited to, devices like a magnetic disk drive, floppy disk drive, tape drive, Jaz drive, Zip drive, LS-60 drive, flash memory card, or memory stick. In addition, the disk storage can include storage media separately or in combination with other storage media including, but not limited to, an optical disc drive such as a compact disc ROM device (CD-ROM), compact disc recordable drive (CD-R Drive), compact disc rewritable drive (CD-RW Drive), or a digital versatile disc ROM drive (DVD-ROM). To facilitate the connection of the disk storage devices to the system bus, a removable or non-removable interface may be employed.

It is to be appreciated that the computer system 210 may include software that acts as an intermediary between users and the basic computer resources described in a suitable operating environment. Such software may include an operating system. The operating system, which can be stored on the disk storage, may act to control and allocate resources of the computer system. System applications may take advantage of the management of resources by the operating system through program modules and program data stored either in the system memory or on the disk storage. It is to be appreciated that various components described herein can be implemented with various operating systems or combinations of operating systems.

A user may enter commands or information into the computer system 210 through input device(s) coupled to the I/O interface 251. The input devices may include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processor through the system bus via interface port(s). The interface port(s) include, for example, a serial port, a parallel port, a game port, and a USB. The output device(s) use some of the same types of ports as input device(s). Thus, for example, a USB port may be used to provide input to the computer system and to output information from the computer system to an output device. An output adapter may be provided to illustrate that there can be some output devices like monitors, displays, speakers, and printers, among other output devices that may require special adapters. The output adapters may include, by way of illustration and not limitation, video and sound cards that provide a means of connection between the output device and the system bus. It should be noted that other devices and/or systems of devices, such as remote computer(s), may provide both input and output capabilities.

The computer system 210 can operate in a networked environment using logical connections to one or more remote computers, such as cloud computer(s), or local computers. The remote cloud computer(s) can be a personal computer, server, router, network PC, workstation, micro-processor-based appliance, peer device, or other common network node, and the like, and typically includes many or all of the elements described relative to the computer system. For purposes of brevity, only a memory storage device is illustrated with the remote computer(s). The remote computer(s) may be logically connected to the computer system through a network interface and then physically connected via a communication connection. The network interface may encompass communication networks such as local area networks (LANs) and wide area networks (WANs). LAN technologies may include Fiber Distributed Data Interface (FDDI), Copper Distributed Data Interface (CDDI), Ethernet/IEEE 802.3, Token Ring/IEEE 802.5 and the like. WAN technologies may include, but are not limited to, point-to-point links, circuit-switching networks like Integrated Services Digital Networks (ISDN) and variations thereon, packet-switching networks, and Digital Subscriber Lines (DSL).

In various aspects, the computer system 210 of FIG. 6, the imaging module 238 and/or visualization system 208, and/or the processor module 232 of FIGS. 5-6, may comprise an image processor, image-processing engine, media processor, or any specialized digital signal processor (DSP) used for the processing of digital images. The image processor may employ parallel computing with single instruction, multiple data (SIMD) or multiple instruction, multiple data (IMD) technologies to increase speed and efficiency. The digital image-processing engine can perform a range of tasks. The image processor may be a system on a chip with multicore processor architecture.

The communication connection(s) may refer to the hardware/software employed to connect the network interface to the bus. While the communication connection is shown for illustrative clarity inside the computer system, it can also be external to the computer system 210. The hardware/software necessary for connection to the network interface may include, for illustrative purposes only, internal and external technologies such as modems, including regular telephone-grade modems, cable modems, and DSL modems, ISDN adapters, and Ethernet cards.

Figure 7:
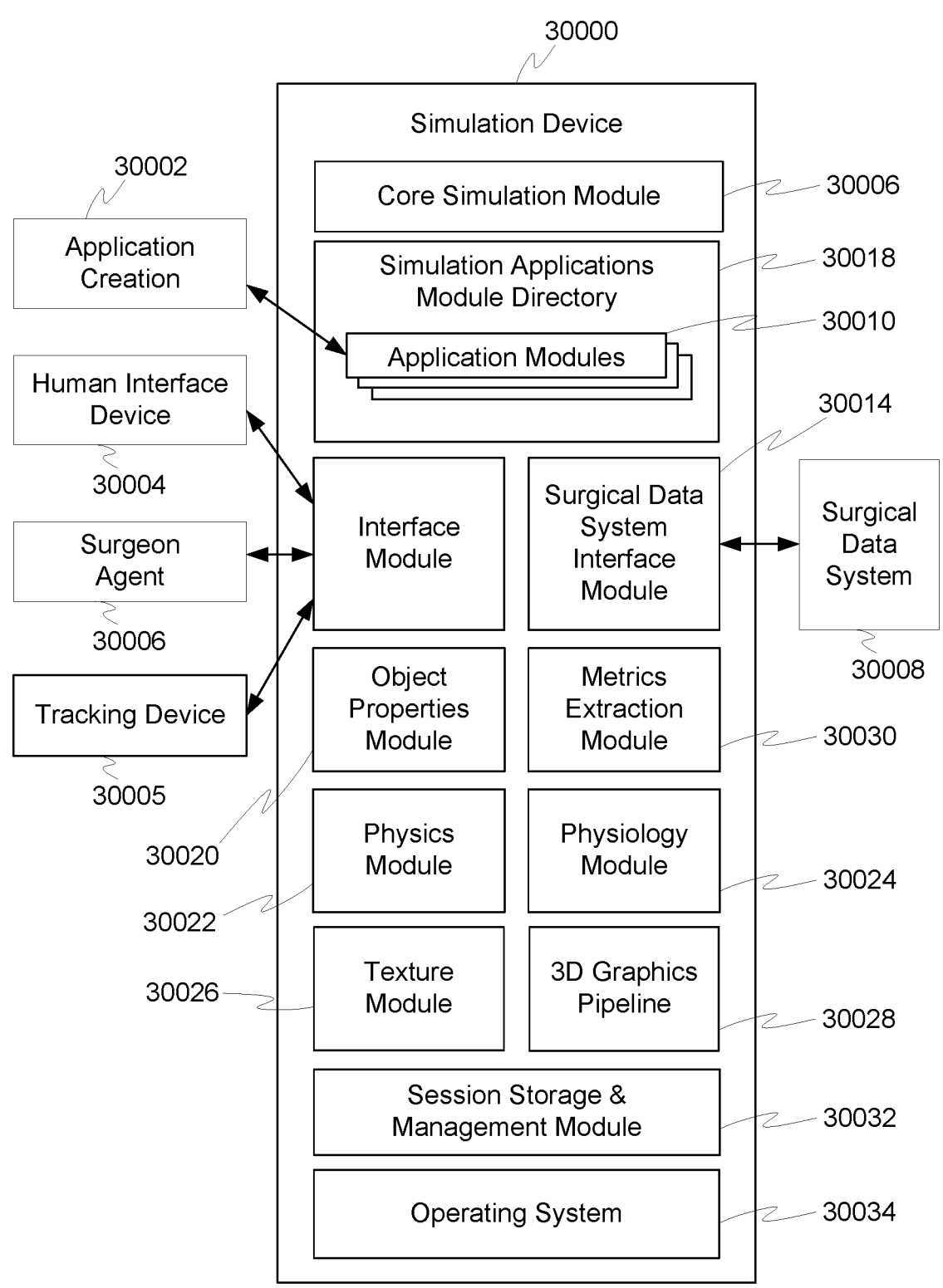
FIG. 7. is a block diagram of an example surgical simulator system.

FIG. 7. is a block diagram of an example surgical simulator system. The surgical simulator system may include a simulation device 30000. The surgical simulator system may include an application creation device 30002, a human interface device 30004, a surgeon agent device 30006, and/or a surgical data system 30008.

The simulation device 30000 may provide core simulation functionality. For example, the loading/running of one or more simulations, the reception and processing of user control information input, the generation and transmission of visual, audible, and/or haptic information output, the collection of simulation operation and activity information, and the primary simulation cycle processing may be performed by the simulation device 30000.

The application creation device 30002 may provide simulation authoring functionality. Individual simulation applications may be stored as application modules 30010 at the simulation device 30000. The application modules 30010 may be created, modified, and/or deleted by the application creation device 30002. The application modules 30010 may include computer readable and/or executable instructions to direct an operation of the simulation device 30000. For example, the application modules 30010 may include any filetype suitable for storing information to run a surgical simulation, for example, simulation scripts, programming code, structure data files such as Extensible Markup Language (XML) files, database files, and the like.

The application creation device 30002 may include a graphical user interface with controls to author application modules 30010. The application creation device 3002 may communicate with the simulation device 30000 to retrieve, modify, and/or load application modules 30010 for simulation operation. For example, the graphical user interface may include interface structures to allow a user to select simulation activities, to input various simulation parameters, to set simulation objectives, and to confirm simulation execution. The application creation device 30002 may be provided as a stand-alone device and/or integrated with one or more other devices of the surgical simulation system, such as integrated with the simulation device 30000 for example.

The human interface device 30004 may include any hardware, software, and/or combination thereof that enables a human user to interact with a simulation provided by the simulation device 30000. The human interface device 30004 may enable a user to provide control input to the simulation device 300000 and/or to receive output information (such as visual, audible, and/or haptic information) from the simulation device 30000. In one example, the human interface device 30004 may include a traditional desktop computer.

The human interface device 30004 may include suitable physical equipment. For example, the human interface device 30004 may include physical equipment that mimic physically and/or virtually aspects of a surgical procedure. For example, such equipment may include bench-top units, part-task virtual reality units, high fidelity virtual reality units, high fidelity full-size patient units, suite units, high fidelity full operating room units, full physics virtual reality units, surgical robot console units, and the like. For example, the human interface device 30004 may include devices such as the computer-based simulator interfaces disclosed by Gallager et al, "Simulations for Procedural Training," Fundamentals of Surgical Simulation, Principles and Practice, Springer (2012).

The human interface device 30004 may include physical equipment that mimics, physically and/or virtually, surgical instruments. For example, the human interface device 30004 may include physical devices that mimic surgical instruments, appliances, and consumables, such as access equipment, such as trocars, hand-access ports, insufflation needles, and guiding sheaths; adjunctive hemostats, such as patches, gelatins, and powders; craniomaxillofacial appliances, like distractors and plates; balloons and inflators; catheters, like diagnostic catheters, access catheters, vascular catheters, and therapeutic catheters; energy sealing and dissecting devices, like tissue sealers, shears, blades, and forceps; orthopedic equipment, like reduction wires, compression screws, plates, implants, drills, burrs, rods, and connectors; ligation instruments, like open and endoscopic clip appliers; microwave ablation equipment; ancillary endoscopic instruments, like drains, sutures, ligature, needle holders, retrievers, and suture clips; surgical stapling equipment, like open staplers, endoscopic staplers, cutter staplers, powered staplers, circular staplers, vascular staplers, linear staplers, staple cartridges, and staple line reinforcement applicators; wound closure materials, like suture, adhesives, needles, and knotless tissue control devices; imaging devices, like minimally invasive imaging devices; and the like. For example, the human interface device 30004 may include virtual reality handheld controllers, that when operated with a virtual reality headset, mimics the surgical instruments, appliances, and consumables, such as those disclosed above.

The human interface device 30004 may include a display that communicates visual representations of the simulation to the user. The human interface device 30004 may include a computer display. The human interface device 30004 may include a virtual reality headset display. For example, the virtual reality headset display may be used display the surgical environment, such as that disclosed in FIG. 2, herein. A user with such a virtual reality headset display may view and/or interact with any of the elements in the surgical operating room 116, including, for example, the patient, the robotic system 110, the surgeon's console 118, the surgical robotic hub 122, one or more surgical tools 117, the imaging device 124, the patient side cart 120, one or more displays 119, 107, 109, and the like.

The human interface device 30006 may present visual information that represents the point of the view of the surgeon. The human interface device 30006 may present visual information from a simulated imaging device, such as an arthroscope, angioscope, bronchoscope, choledochoscope, colonoscope, cytoscope, duodenoscope, enteroscope, esophagogastro-duodenoscope (gastroscope), endoscope, laryngoscope, nasopharyngo-neproscope, sigmoidoscope, thoracoscope, ureteroscope, and their related instruments, controls, and the like. The human interface device 30006 may present visual information from a simulated supplemental intra-operative imaging equipment, like computed tomography (CT) units, magnetic resonance imaging (MRI) units, image-guided surgery units, intra-operative ultrasound units; fluoroscopy units, and the like. Such point-of-view visual information, surgical imaging information, and supplemental intra-operative imaging information may be displayed in any combination to the user suitable for the simulation's operation. For example, such information may be presented to the user as a single full-screen view, a tiled window view, a picture-in-a-picture view, or registered to a simulated display unit in a virtual reality view.

The human interface device 30004 may include a physical and/or virtual reality surgical robot surgeon console. For example, an example surgeon-console-like human interface device 30004 may include a display, such as a stereo vision display and control inputs, including hand-held manipulators, foot pedals, and the like. For example, the surgeon-console-like human interface device 30004 may include an interface of the surgeon's console 118, disclosed herein. The human interface device 30004 may enable voice controls via, for example, a microphone and speech recognition functionality. The human interface device 30004 may provide audible feedback via, for example, a speaker. The human interface device 30004 may provide haptic feedback via, for example, vibration, force feedback, air vortex rings, and ultrasound techniques.

As implemented, the human interface device 30004 may be provided as a stand-alone device and/or integrated with one or more other devices of the surgical simulation system, such as integrated with the simulation device 30000 for example. The simulation device 30000 may include an interface module 30012 to communicate with the human interface device 30004. In an example, human interface device 30004 may be integrated into one or more elements of the computer-implemented interactive surgical system 100. For example, the human interface device 30004 may be integrated into the computer system 210. For example, the human interface device 30004 may be integrated into the hub 106. For example, the human interface device 30004 may be integrated into the visualization system 108. The interface module 30012 may communicate with the one or more elements of the computer-implemented interactive surgical system 100 via the surgical data system interface module 30014 for example.

In an embodiment, more than one human interface device 30004 may concurrently engage with the simulation device 30000. For example, a multi-person simulation application The surgeon agent device 30006 may include any hardware and/or software suitable for providing a computer-based control and response to the input and output of the simulation device 30000. The surgeon agent device 30006 may include a computer process that mimics human input to the simulation device 30000. For example, the surgeon agent device 30006 may be able to record and register control inputs, such as basic instrument manipulation. The surgeon agent device 30006 may include a computer process that can access a input/output application programming interface (API) of the simulation device 30000. For example, the API may reveal one or more input/output functions that may be directed according to the surgeon agent device 3006. The functions may include granular manipulation and physics-based input/output functions, such as functions that directly control the location and movement of instruments. The functions may include less granular surgical-activity-based input/output functions, such as a ligation activity, a suturing activity, a stapling activity, and the like. The functions may include less granular surgical task and/or stage-based input/output functions, such as surgical access function, organ mobilization function, and the like. Each function may include parameter consistent with its level of granularity. The parameters may provide specific details to direct the operation of the function within the simulation. The surgeon agent 30006 may include functionality for generating and operating multiple simulation runs. For example, a user may wish to estimate the duration of various suturing techniques. A surgeon agent device 30006 may be used to script the simulation of any number of different techniques, each of which can be run via the simulation device, and the metrics collected by the simulation device may be used to estimate the difference in durations.

The surgeon agent device 30006 may be provided as a stand along device and/or integrated with one or more other devices of the surgical simulation system, such as integrated with the simulation device 30000 for example. The simulation device 30000 may include an interface module 30012 to communicate with the surgeon agent device 30006. For example, the surgeon agent device 30006 may be integrated as a module of the simulation device 30000. For example, the surgeon agent device 30006 may be integrated into an application module 30010 of the simulation device.

The surgical data system 30008 may include any hardware and/or software suitable for providing external, structured surgical information and functionality to the simulation device 30000. The surgical data system 30008 may include the structure and/or functions described in connection with FIGS. 1-6 herein. For example, the surgical data system 30008 may include one or more elements of a computer-implemented interactive surgical system 100. The surgical data system 30008 may include, for example, a surgical hub 106. For example, the simulation device 30000 include a surgical data system interface module 30014 that enables communication with the surgical hub 106 via the surgical hub's communication module 130. The surgical data system 30008 may include, for example, on or more surgical data repositories. For example, the surgical data system 30008 may include the computer system 210 located in the surgical theater. For example, the surgical data system 30008 may include the remote server 213 in the cloud 204.

A surgical data system 30008, such as the surgical hub 106 for example, may provide data to the simulation device 30000 and/or the application creation device 30002. For example, the data may include any surgical data collected and/or generated by the surgical hub 106. Also for example, the simulation device 30000 may receive similar data directly from any of the networked devices disclosed in FIGS. 1-6. Such data may include information about a live surgical procedure, for example. Such data may include information about a past surgical procedure. Such data may include information about future, scheduled surgical procedures.

Information about the surgical procedures may include information about the patient, the staff, the procedure as planned, the procedure as experienced, and post-operative activity including patient outcomes. For example, the information received and used by the simulation device may include patient records, patient imaging, models of patient anatomy, patient lab results, patient medical history, and the like. For example, the information received and used by the simulation device may include a staff manifest for a procedure, details about the past procedures of the specific staff members, staff metrics, experience, recent scheduling and workload, and historical surgical activity, such instrument use statistics, procedure duration, and the like. For example, the information received and used by the simulation device may include procedure plans, equipment and inventory information, pull-lists, checklists, procedure plan analysis and recommendations. For example, the information received and used by the simulation device may include any data collected or generated during a live procedure, such as procedure progress, milestones, patient information, vitals, operating theater setup, staff movement, imaging, instrument use, surgical technique, such as that captured by video, recorded manually, and/or inferred from smart-instrument reporting for example, duration, abnormal event reporting, and the like. Any data captured during a live procedure may also be stored and made available as a past procedure. For example, the information received and used by the simulation device may include post-operative records, patient recovery information, and patient outcome information, post-operative diagnostic information, such as labs, imaging, etc., The simulation device 30000 may include any computer or processing platform suitable for executing one or more simulations. The simulation may include a computer-modeled environment of a surgical procedure. For example, the simulation may include a model of a patient's anatomy and/or physiology. For example, the simulation may include a model of the actions and/or instruments of one or more healthcare professionals, such as the actions of a surgeon, nurse, other doctor, technician, or the like.

The simulation device 30000 may include one or more functional modules. Each module may include hardware, software, or a combination thereof that enable functionality of the module. One or more modules, operating in concert, may represent a computer framework on which a simulation of a medical procedure may be executed. The modules may include hardware elements, such as a computer processing unit, a graphics processing unit, a field-programmable gate array (FPGAs), communications hardware, memory, and the like. The modules may include software elements that when executed by a processor cause the module to perform certain functions.

The simulation device may include a core simulation module 30016, a simulation applications module directory 30018, the interface module 30012, an object properties module 30020, a physics module 30022, a physiology model 30024, a texture model 30026, a 3D graphics pipeline 30028, the surgical data system interface module 30014, a metrics extraction module 30030, a session storage and management module 30032, for example. The simulation device may include an operating system module 30034.

The core simulation model 30016 may provide primary simulation functionality of the simulation device 30000. For example, the core simulation module 30016 may include code for initializing a simulation, for communicating and interacting with other modules of the simulation device 30000, and/or for managing architectural level simulation parameters. For example, the core simulation module 30016 may include a master event clock to provide time alignment and/or coordination of the operation of the modules of the simulation device 30000. For example, the core simulation module 30016 may establish the overall simulation frame rate.

The core simulation module 30016 may include core for providing a master simulation cycle. The core simulation module 30016 may run one or more iteration of the master simulation cycle. Each iteration of the master simulation cycle may represent an individual time slice for simulation. In an example, the core simulation module 30016 may run the master simulation cycle according to the flow disclosed in FIG. 10.

The simulation applications module directory 30018 may manage the storing, retrieving, and/or linking of the one or more application modules 30010. Each application module 30010 may include code that directs the application-level aspects of a simulation. For example, an application module 30010 may include the functionality to provide a simulation of specific anatomy, of specific teaching scope, of specific equipment, or the like. In an example simulation device 30000, an application-specific simulation device 30000 may operate with a single application module 30010 with or without a simulation application module directory 30010. The simulation application module directory 30018 may operate based on interaction with the core simulation module 30016 and/or the application creation device 30002.

The interface module 30012 may provide functionality for interacting with the human interface device 30004 and/or the surgeon agent device 30006. For example, the interface module 30012 may include one or more drivers to translate information received from human interface device 30004 into software commands, interrupts, and the like. For example, the interface module 30012 may include a software application programming interface (API) for interacting with the surgeon agent 30006. The interface module 30012 may provide information received from the human interface module 30004 and/or the surgeon agent device 30006 to other modules of the simulation device 30000. For example, the interface module 30012 may receive a control input from the human interface module 30004 and/or the surgeon agent device 30006 that represents movement of a simulated instrument and provide that information to one or more other modules of the simulation device 30000 so the movement may be represented in the simulation.

The interface module 30012 may provide the API to enable a more granular interaction with the surgeon agent device 30006. For example, the API may provide an inter-face to receive simulation parameters and simulation settings from the surgeon agent device 30006. Such simulation parameters and/or simulation settings may be like those input by the user via the application creation device 30002, for example. For example, the surgeon agent device 30006 may be enabled to run one or more computer-controlled simulation trials through the simulation device 30000. For example, the surgeon agent device 30006 may be enabled to run multiple simulations, each with alternative interactions.

The interface module 30012 may send output from the simulation device 30000 to the human interface device 30004 and/or the surgeon agent device 30006. For example, the output may include visual output, haptic output, audio output, and/or structured data output, or the like.

The object properties module 30020 may provide functionality for managing the simulated appearance and/or behavior of objects within in the simulation. Simulated objects may include objects such as anatomy, instrument, equipment, consumables, fluids, and the like. An object's appearance may be managed by object properties, such as location, dimensions, scale, material, parent/child relationships, vertices, faces, interactivity, transparency, trajectory, rendering properties, textures, surface reflectivity, motion blur, layering, and the like. An object's behavior may be managed by object properties, such as physics properties, mass, motion, collision behavior, elasticity, viscosity, surface tension, rigging constraints, hardness, shear strength, tearing behavior, grain, and the like.

The physics module 30022 may provide functionality to calculate the physical responses and/or interaction of objects within the simulation. The physical module may determine such responses and/or interactions according to classical mechanics, fluid mechanics, soft body dynamics, Brownian motion, collision detection, cloth behavior, finite element analysis, and the like. The physics module 30022 may include commercial and/or open-source modules, such as PhysX™, Simulation Open Framework Architecture (SOFA)™, VisSim™, and the like.

The physiology module 30024 may provide functionality to calculate physiological responses and/or interactions of the anatomy and/or patient as a whole in the simulation. The physiology module 30024 may provide physiological models for key organs and/or systems. The physiological models may include mathematical models, statistical models, or the like. For example, the physiology module 30024 may module the patient's vitals to calculate their response and/or interaction to activities performed during the simulation. For example, a circulatory model may calculate blood pressure in response to a severed vessel in the simulation. The physiology module 30024 and the physics module 30022 may coordinate with each other during the calculation of each state of the simulation. For example, blood pressure calculated by the circulatory model may be used to determine fluid dynamics properties calculated by the physics module 30022 and managed by the object properties module 30020.

The texture module 30026 may provide functionality to determine, retrieve, and/or generate the appropriate surfacing of objects within the simulation. The texture module 30026 may include one or more surfacing modalities that may be controlled according to parameters of the simulation. The surfacing modalities may include artificially generated surfaces, surfaces based on real-world imagery, and combinations thereof. The texture module 30026 may coordinate operation with the physics module 30022 to provide accurate haptic feedback to the user via the user interface module 30012.

The 3D graphics pipeline 30028 may provide functionality for visual rendering of the simulation environment. The 3D graphics pipeline 30028 may receive object properties and a perspective. The 3D graphics pipeline 30028 may determine the visualization to be presented to the user that represents the objects in 3D space as viewed from the camera perspective. The 3D graphics pipeline 30028 may determine geometric aspects of the rendering, such as lighting, projection, clipping, view transformation, and the like. The 3D graphics pipeline 30028 may determine rasterization aspects of the rendering, such as fragmentation, pixel shading, vertex shading, geometry sharing, texture filtering, and the like. The 3D graphics pipeline 30028 may coordinate with the texture module 30026 to provide accurate visual feedback to the user via the interface module 30012.

The surgical data system interface module 30014 may provide interactive connectivity to one or more elements of computer-implemented interactive surgical system 100. Information from the one or more elements of the computer-implemented interactive surgical system 100 may be communicated via the surgical data system interface module 30014 to one more modules of the simulation device 30000 to influence operation of a simulation. For example, the surgical data system interface module 30014 may receive information about a surgical procedure an communicate it to a corresponding application module 30010. For example, the surgical data system interface module 30014 may receive information about an instrument and communicate it to the object properties module 30020. For example, the surgical data system interface module 30014 may receive information about a patient and communicate to the physiology module. For example, the surgical data system interface module 30014 may receive information about tissue imaging and communicate it to the texture module 30026.

Information from the modules of the simulation device 30000 may be provided, via the surgical data system interface 30014, to one or more elements of the computer-implemented interactive surgical system 100. For example, one or more elements of the computer-implemented interactive surgical system 100 may receive statistics related to a simulated procedure plan from the metrics extraction module 30030. For example, one or more elements of the computer-implemented interactive surgical system 100 may receive replayed simulation visualization procedure plan from the session storage and management module 30032. For example, the surgical data system interface module 30014 may provide a communications pathway between the interface module 30012 and one or more elements of the computer-implemented interactive surgical system 100. For example, a surgeon during a live surgical procedure may access simulation information and/or operate a simulation from the operating theater. For example, a surgeon may use the surgeon console 118 to access and/or interact with a simulation that corresponds to the live surgical procedure.

The metrics extraction module 30014 may provide recording functionality of various parameters related to the operation of the simulation. For example, the metrics extraction module 30014 may record metrics related to the simulation as a whole, such as duration, number of activities, number of movements, complexity of movements, staff employed, staff movement, equipment and/or instrument changes, etc. For example, the metrics extraction module 30014 may record metrics related to a particular aspect of the simulation, such as simulated patient vitals, complications, collisions, bleeding, etc. The metrics extraction module 30014 may maintain a master log of metric-related events during a simulation. For metrics extraction module

30014 may record metric-related events according to a configuration from the application module 30010 employed for the simulation.

The session storage and management module 30032 may provide management functionality of the main simulation run-record. For example, the session storage and management module 30032 may store the information to enable a simulation to be rerun, viewed, and/or analyzed in its entirety. The session storage and management module 30032 may store the information about each input, simulation state, and output, such as the input, simulation state, and output disclosed with regard to FIG. 10. The session storage and management module 30032 may enable a previous simulation to be recalled, copied, and initialized with new user input. To illustrate, a surgeon in training may recall a simulation run by an experienced surgeon, pause the simulation at a critical step, and attempt that step on her own. The session storage and management module 30032 may provide overlay functionality between various runs of a particular simulation. Such overlays may highlight similarities and differences and may enhance training.

The operating system module 30034 may manage the hardware and/or software resources for the simulation device 30000. The operating system module 30034 may provide common computing system-level services for the other modules of simulation device 30000. For example, the operating system module 30034 may provide hardware input and output handling, memory allocation, hardware interrupt handling, software interrupt handling, thread processing, single task handling, multi-task handling, and the like. The simulation device 30000 may be a real-time computing device. The operating system module 30034 may include a real-time operating system. For example, the operating system module 30034 may be driven by the events and frame rate established by the core simulation module 30016.

Figure 8:
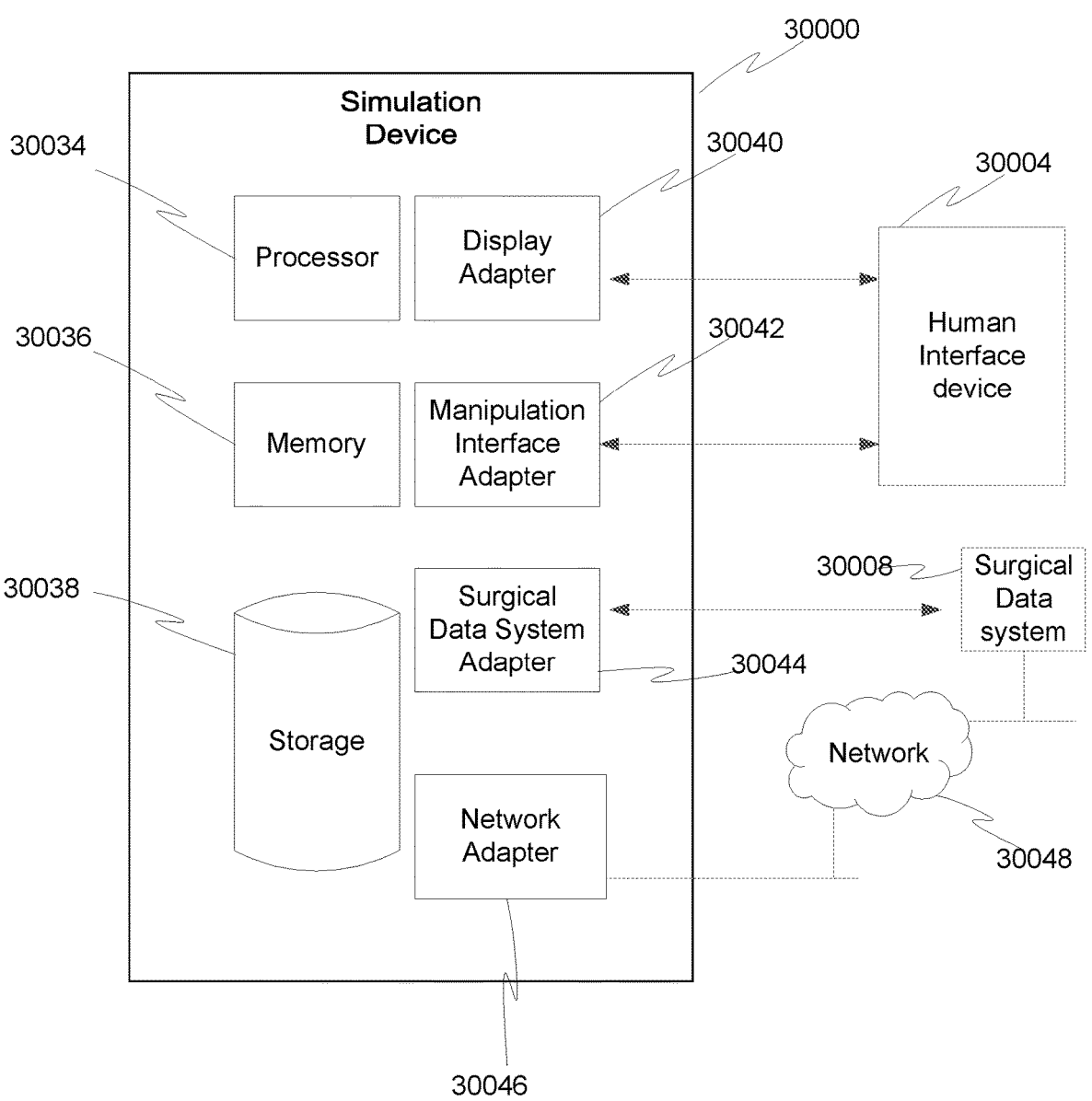
FIG. 8 is a block diagram of an example surgical simulator system.

FIG. 8 is a block diagram of an example surgical simulator system. The simulation device 30000 is depicted with an example hardware architecture. For example, the simulation device 30000 may include a processor 30034, a memory 30036, a storage 30038, a display adapter 30040, a manipulation interface adapter 30042, a surgical data system adapter 30044, and/or a network adapter 30046. One or more of the processor 30034, a memory 30036, a storage 30038, a display adapter 30040, a manipulation interface adapter 30042, a surgical data system adapter 30044, and/or a network adapter 30046 may be used to enable operation of the modules of the simulation device 30000 disclosed herein.

The processor 30046 may include computer processing unit, graphics processing unit, any suitable microcontroller, microprocessor, field programmable gate array (FPGA), application specific integrated circuit (ASIC), or the like, and/or any combination thereof that is suitable for processing and delivering a 3D simulated environment for interaction with a computer agent and/or human user. In one example, the processor 30046 may include one or more processing units. The processor 30046 may be a processor of any suitable depth to perform the digital processing requirements disclosed herein. For example, the processor 30046 a 32-bit processor, a 64-bit processor, a 128-bit processor, or the like.

Such processors may comprise, or may be in communication with, media, for example computer-readable media, that may store instructions that, when executed by the processor, can cause the processor to perform the steps described herein as carried out, or assisted, by a processor. Embodiments of computer-readable media may comprise, but are not limited to, an electronic, optical, magnetic, or other storage device capable of providing a processor, such as the processor in a web server, with computer-readable instructions. Other examples of media comprise, but are not limited to, a floppy disk, CD-ROM, magnetic disk, memory chip, ROM, RAM, ASIC, configured processor, all optical media, all magnetic tape or other magnetic media, or any other medium from which a computer processor can read. The processor, and the processing, described may be in one or more structures, and may be dispersed through one or more structures. The processor may comprise code for carrying out one or more of the methods (or parts of methods) described herein.

The memory 30036 may include any component or collection of components suitable for storing data. For example, the memory 30036 may include volatile memory and/or nonvolatile memory. The memory 30036 may include random-access memory (RAM), read-only memory (ROM), erasable programmable read-only memory (EPROM), (electrically erasable programmable read-only memory) EEPROM, flash memory, or the like.

The storage 30038 may include any component or collection of components suitable for storing large quantities of data. For example, storage 30038 may include hard disk drives (HDD), solid state drives (SSD), network-attached storage (NAS), or the like. The storage 30038 may include a database structure and/or a database management system (DBMS).

The display adapter 30040 may include any component or collection of components suitable for outputting the visual representation of a 3D simulation environment. For example, the display adapter 30040 may include a graphics card, a display card, a graphics adapter, or the like. The display adapter 30040 may be used to generates a feed of output images to a display device, such as a display of the human interface device 30004. The display adapter 30040 may include a graphics processing unit (GPU). The display adapter 30040 may include hardware to render a graphics pipeline, for example. The manipulation interface adapter 30042 may include any component or collection of components suitable for receiving manipulation information from the human interface device and/or outputting feedback information to the human interface device. For example, the manipulation interface adapter 30042 may receive motion tracking information from a virtual reality headset and in turn, manipulate the view being displayed to the user. For example, the manipulation interface adapter 30042 may receive control input indicative of a user manipulating a surgical instrument and, in turn, output haptic feedback to the user's handheld device. For example, the manipulation interface adapter 30042 may receive control information from a traditional desktop keyboard and mouse. The manipulation interface adapter may include input/output hardware such as serial input/output ports, parallel input/output ports, universal asynchronous receiver transmitters (UARTs), discrete logic input/output pins, analog-to-digital converters, digital-to-analog converters, universal serial bus (USB) ports, USB-C ports, FireWire ports, High Performance Parallel Interface (HIPPI), Thunderbolt port, Yapbus, Ethernet, Gigabit Ethernet, and/or any other suitable peripheral interface technology.

The surgical data system adapter 30044 may include any component or collection of components suitable for communicating with the surgical data system 30008. The surgical data system adapter 30044 may include communications hardware to establish a physical channel between the simulation device 30000 and the surgical data system 30008. For example, the surgical data system adapter 30044 may include a communication port such as, a USB port, USB-C ports, FireWire ports, HIPPI port, Thunderbolt port, Yapbus port, Ethernet port, Gigabit Ethernet port, and/or any other suitable peripheral interface. The surgical data system adapter 30044 may include hardware, software, and/or a combination thereof to establish a logical channel between the simulation device 30000 and the surgical data system 30008 over the network adapter 30046 and the network 30048.

The network adapter 30046 may include any component or collection of components suitable for communication over a network, such as network 30048 for example. The network adapter 30046 may enable communication over networks such as local area networks (LANs), wide area networks (WANs), and/or mobile networks. LAN technologies may include Fiber Distributed Data Interface (FDDI), Copper Distributed Data Interface (CDDI), Ethernet/IEEE 802.3, Token Ring/IEEE 802.5, Wi-Fi/IEEE 802.11, and the like. WAN technologies may include, but are not limited to, point-to-point links, circuit-switching networks like Integrated Services Digital Networks (ISDN) and variations thereon, packet-switching networks, and Digital Subscriber Lines (DSL). The mobile networks may include communication links based on one or more of the following mobile communication protocols: GSM/GPRS/EDGE (2G), UMTS/HSPA (3G), long term evolution (LTE) or 4G, LTE-Advanced (LTE-A), new radio (NR) or 5G, etc.

In an embodiment, the network adapter 30046 may include a wireless network adapter, such as a 5G network adapter. Such a 5G network adapter 30046 may use a 5G New Radio (NR) transceiver to provide enhanced mobile broadband (eMBB) with ultra-reliable and low latency communications (URLLC). Such a 5G network adapter 30046 may use wireless bands, such as higher wireless bands like the 3.5 Ghz-7 Ghz and/or the 24 GHz-48 GHz bands. The network 30048 servicing such a 5G network adapter 30046 may include a public wireless network, a semi-private (e.g., network slicing-based) network, and/or a fully private wireless network.

Figure 9:
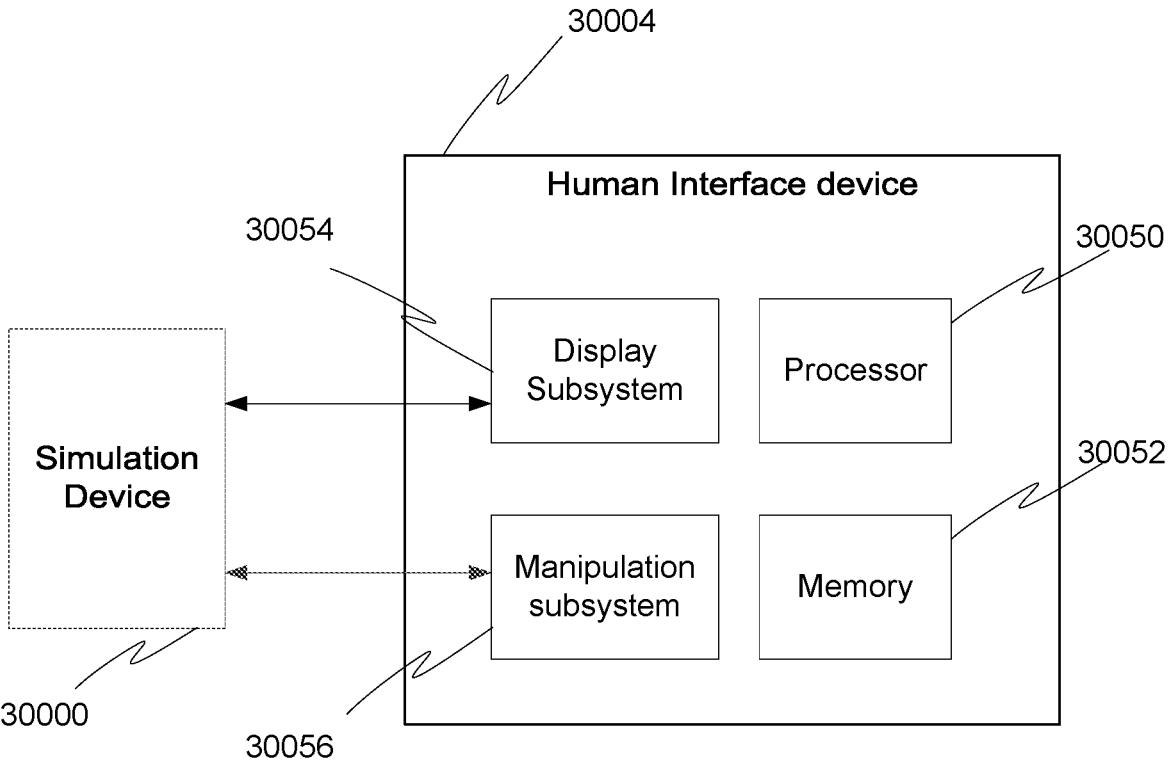
FIG. 9 is a block diagram depicting an example surgical simulator user interface device.

FIG. 9 is a block diagram depicting an example surgical simulator human user interface device 30004. The human user interface device 30004 is depicted with an example hardware architecture. For example, the human user interface device 30004 may include a processor 30050, a memory 30052, a display subsystem 30054, and/or a manipulation subsystem 30056.

The processor 30050 may include computer processing unit, graphics processing unit, any suitable microcontroller, microprocessor, field programmable gate array (FPGA), application specific integrated circuit (ASIC), or the like, and/or any combination thereof that is suitable for handling the processing associated with displaying visual information received from the simulation device 30000, processing manipulation information for sending to the simulation device, processing feedback information received from the simulation device 30000, and the like. The processor 30050 may include a microcontroller to interface with one or more local sensors to sense control manipulation from the user and/or to interface with one or more local actuators to provide feedback from the user.

Such processors may comprise, or may be in communication with, media, for example computer-readable media, that may store instructions that, when executed by the processor, can cause the processor to perform the steps described herein as carried out, or assisted, by a processor. Embodiments of computer-readable media may comprise, but are not limited to, an electronic, optical, magnetic, or other storage device capable of providing a processor, such as the processor in a web server, with computer-readable instructions. Other examples of media comprise, but are not limited to, a floppy disk, CD-ROM, magnetic disk, memory chip, ROM, RAM, ASIC, configured processor, all optical media, all magnetic tape or other magnetic media, or any other medium from which a computer processor can read. The processor, and the processing, described may be in one or more structures, and may be dispersed through one or more structures. The processor may comprise code for carrying out one or more of the methods (or parts of methods) described herein.

The memory 30036 may include any component or collection of components suitable for storing data. For example, the memory 30036 may include volatile memory and/or nonvolatile memory. The memory 30036 may include random-access memory (RAM), read-only memory (ROM), erasable programmable read-only memory (EPROM), (electrically erasable programmable read-only memory) EEPROM, flash memory, or the like.

The display subsystem 30054 may include any component or collection of components suitable for displaying visual representations of a 3D simulation from the simulation device 30000 to a user. The display subsystem may include display hardware such as a monitor, a digital projector, a smart phone, a digital headset, a virtual reality headset, a stereoscopic display, a robotic surgery surgeon's console display, a surgical display unit, a surgical microscope, and the like.

The manipulation subsystem 30056 may include any component or collection of components suitable for collecting manipulation controls from the user to send to the simulation device 30000 and/or providing feedback information, received from the simulation device 30000, to the user. Manipulation from the user may include any interface with sensors that engage with the user, for example, engaging to indicate a user's intent in the simulation. For example, the interfaces may include keyboards, mice, joysticks, physical equipment that mimics the size, shape, and operation of actual surgical instruments, virtual reality hand-held controllers, smart gloves, motion sensing systems (such as hand tracking systems, for example), a robotic surgery surgeon's console manipulators and/or controls, a physical unit that mimics the size, shape, and operation of an actual robotic surgery surgeon's console manipulators and/or controls, and the like. For example, the interface may include a point of view sensor, such as an accelerometer, in a headset to indicate a user's point of view within the simulation.

Feedback from the simulation device 30000 may include any interface with an actuator that provides sensory input to the user. For example, the feedback may include haptic feedback, force feedback, temperature feedback, moisture feedback, audio feedback, olfactory feedback, and the like. For example, a force feedback and/or haptic actuator in the manipulator of a robotic surgery surgeon's console may be used to simulate the feedback the user would feel if operating such a manipulator in a live procedure. For example, a force feedback and/or haptic actuator in a user device that mimics the size, shape, and operation of actual surgical stapler may be used to simulate the feedback the user would feel if operating such a device on live tissue, including force feedback when engaging the tissue and firing the stapler for example.

Figure 10:
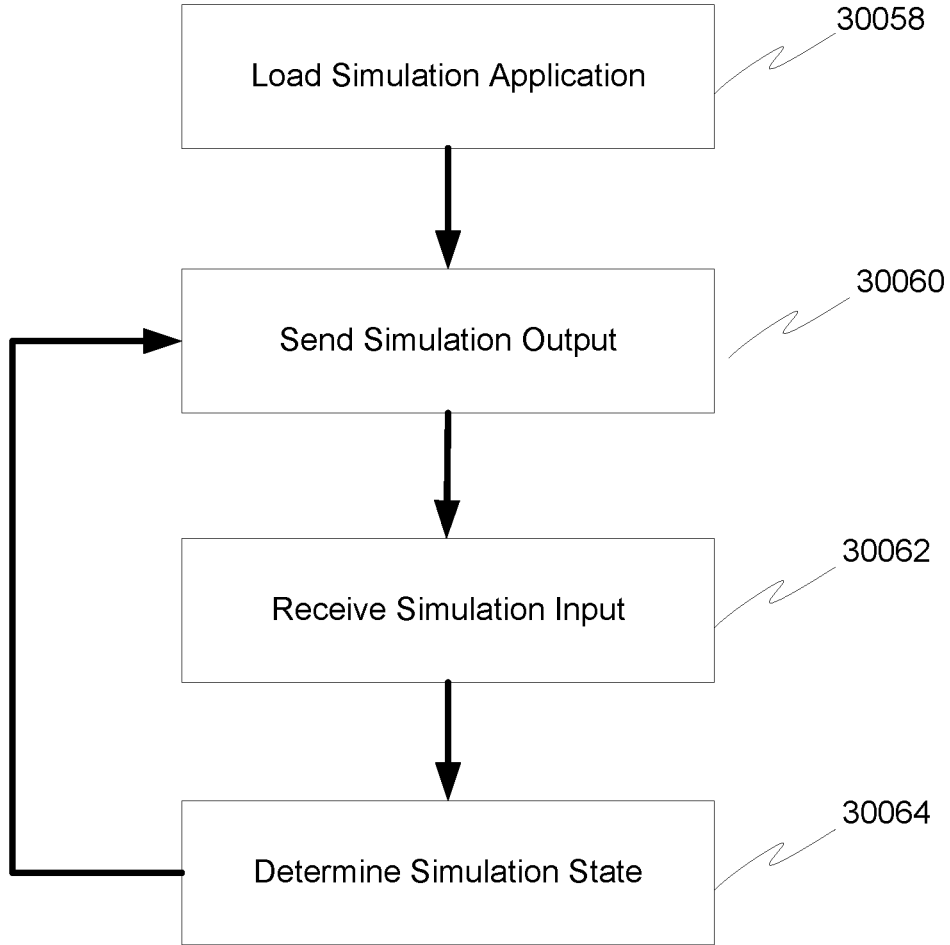
FIG. 10 is a flow chart of an example surgical simulator operation.

FIG. 10 is a flow chart of an example surgical simulator operation. At 30058, a simulation application may be loaded. For example, the core simulation module 30016 may cause data associated with a particular application module 30010 to be loaded into memory 30036. The loaded data may include instructions for the processor 30034 to operate a particular simulation. The loaded data may include a procedural plan for the simulation. For example, the procedural plan may be structured as disclosed herein, for example with regard to FIGS. 11A-B. The loaded data may include an initial state for the simulation.

At 30060, the simulation output may be determined and/or sent. For example, the simulation output may be determined and/or sent by the simulation device 30000. Here, the core simulation module 30016 may reference a current state of the simulation (e.g., an initial state and/or a subsequent state). The core simulation module 30016 may engage one or more other modules to process the current state for output. For example, the core simulation module may engage any of the object properties module 30020, the texture module 30026, the application module 30010, the 3D graphics pipeline 30028, the interface module 30012, and/or the surgical data system interface module 30014 to process the current simulation state into information for output. Information related to the output maybe processed and/or stored by the metrics extraction module 30030 and/or the session storage and management module 30032, for example.

In a human-operated simulation session, for example, output information may be sent via the display adapter 30040 and/or the manipulation interface adapter 30042 to the display subsystem 30054 and/or the manipulation subsystem 30056 of the human interface device 30004. In a computer-controlled simulation session, for example, output information may be sent via the interface module 30012 to a surgeon agent 30006. Also for example, in a computer controlled simulation session, output information may be sent (e.g., processed locally) at an application module 30010. In a session accessed via the surgical data system 30008, for example, output information may be sent by the surgical data system interface module 30014 via the surgical data system adapter 30044 and/or the network adapter 30046.

At 30062, simulation input may be received and/or processed. For example, simulation input may be received and/or processed by the simulation device 30000. Here, the core simulation module may engage with the interface device, the surgical data system interface module, and/or the application module 30010 to receive control input. Information related to the input maybe processed and/or stored by the metrics extraction module 30030 and/or the session storage and management module 30032, for example.

In a human-operated simulation session, for example, input information may be sent from a manipulation subsystem 30056 of the human interface device 30004 and received via the manipulation interface adapter 30042. In a computer-controlled simulation session, for example, input information may be sent from a surgeon agent 30006 and received via the interface module 30012. Also for example, in a computer controlled simulation session, input information may be received (e.g., processed locally) at an application module 30010. In a session accessed via the surgical data system 30008, for example, input information may be received via the surgical data system adapter 30044 and/or the network adapter 30046 and initially handled by the surgical data system interface module 30014.

At 30064, a subsequent simulation state may be determined. For example, a subsequent simulation state may be determined from the current simulation state and/or the any received input. The core simulation module 30016 may engage one or more of the other modules of the simulation device 30000 to determine the subsequent simulation state. For example, the code simulation module 30016 may engage the application module, the object properties module, the physics module, the physiology module, and the like. The subsequent simulation state may be determined by operation of the processor 30034. Information related to the input maybe processed and/or stored by the metrics extraction module 30030 and/or the session storage and management module 30032, for example.

At this stage, the process may loop to receiving input at 30060. Each iteration of this flow may represent a corresponding time cycle in the simulation. The framerate of the simulation may be set to a level suitable for the goal of the simulation and the processing capabilities of the surgical simulation device 30000. Lower framerates may enable processing that achieves a live human interaction simulation. Higher framerates may enable greater simulation fidelity. For example, when operating computer-controlled simulations, with a surgeon agent 30006 for example, a higher framerate may be used, even if the higher framerate causes the processing time of the simulation to exceed the real-world time it is simulating.

Figure 11A:
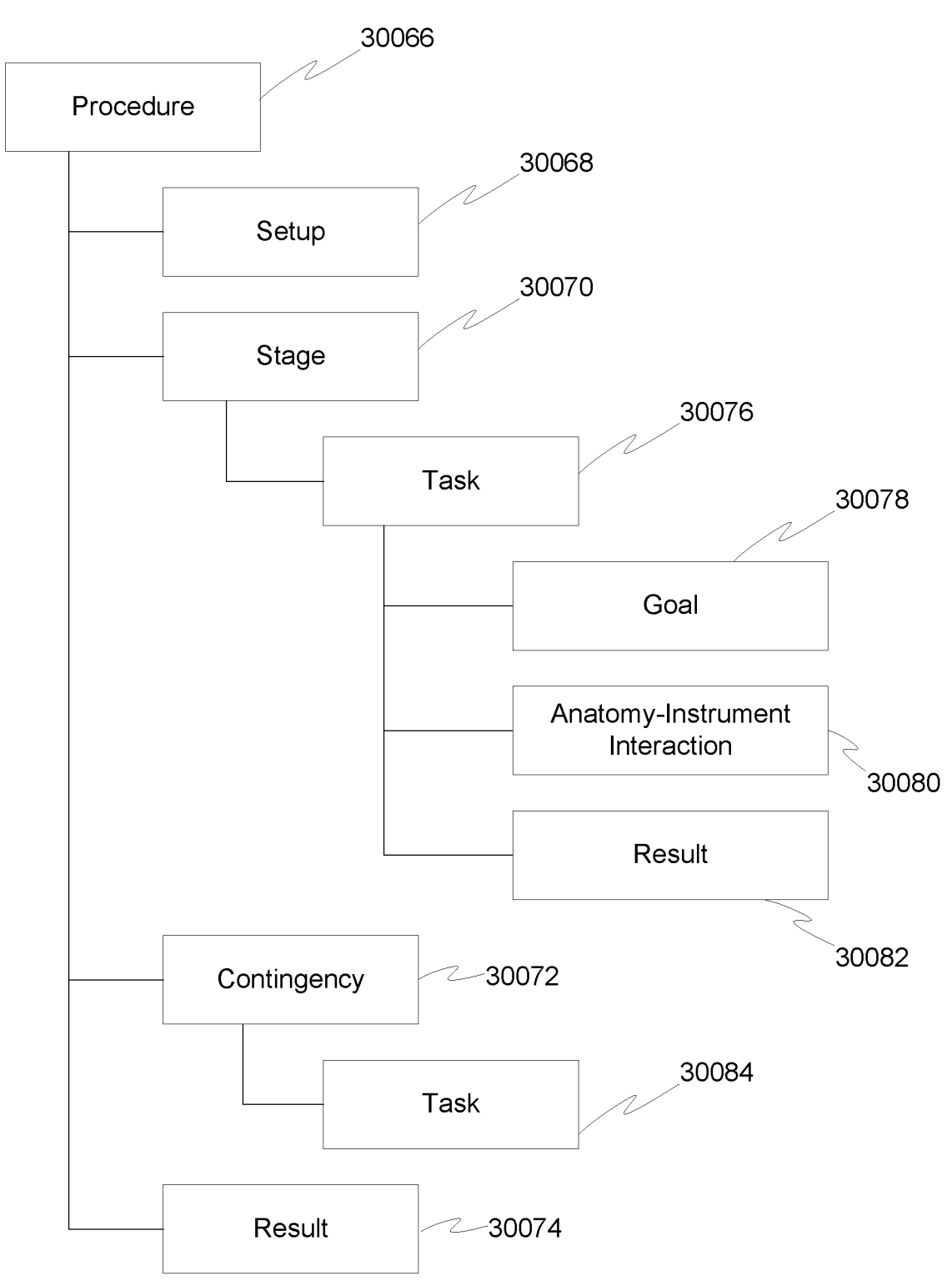
FIGS. 11A-B illustrate example surgical procedural plan data structures for use with a computer-implemented interactive surgical system and/or a surgical simulator.
Figure 11B:
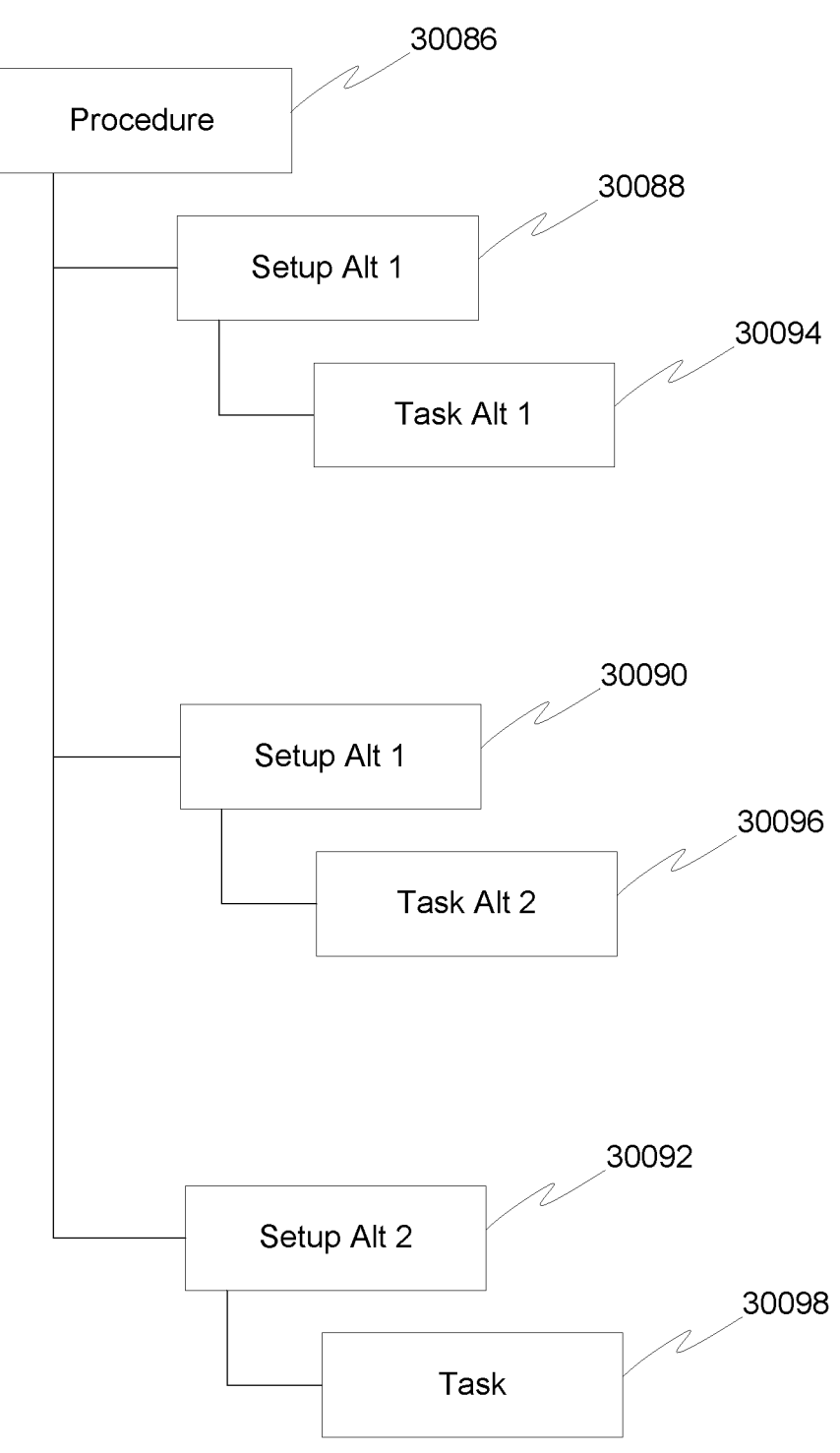

FIGS. 11A-B illustrate example surgical procedural plan data structures for use with a computer-implemented interactive surgical system and/or a surgical simulator. A surgical procedure plan may include information that outlines the staff, equipment, technique, and steps that may be used to perform a surgical procedure. For example, the procedure plan may include a staff manifest indicating what roles and/or what specific health care professionals are to be involved in the procedure. The procedure plan may include a listing of equipment, such as durable surgical equipment, imaging equipment, instruments, consumables, etc. that may be used during the procedure. For example, the procedure plan may include a pick list for a surgical technician to use to assemble the appropriate tools and materials for the surgeon and the surgery when prepping the operating theater. The procedure plan may include information about the procedure's expected technique. For example, the procedure plans for the same surgical goal may include different methods of access, mobilization, inspection, tissue joining, wound closure, and the like.

The procedure plan may reflect a surgeon's professional judgement with regard to an individual case. The procedure plan may reflect a surgeon's preference for and/or experience with a particular technique. The procedure plan may map specific surgical tasks to roles and equipment. The procedure plan may provide an expected timeline for the procedure.

The procedure plan may include one or more decision points and/or branches. Such decision points and/or branches may provide surgical alternatives that are available for particular aspects of the procedure, where selection of one of the alternatives may be based on information from the surgery itself. For example, the choice of one or more alternatives may be selected based on the particular planes of the particular patient's anatomy, and the surgeon may select an alternative based on her assessment of the patient's tissue during the live surgery.

The procedural plan may include one or more contingencies. These may include information about unlikely but possible situations that may arise during the live surgery. The contingencies may include one or more surgical tasks that may be employed if the situation does occur. The contingencies may be used to ensure that adequate equipment, staff, and/or consumables are at the ready during the procedure.

The procedure plan may be recorded in one or more data structures. A procedure plan data structure may be used to record data about a future live surgery, about a completed live surgery, about a future simulated surgery, about a completed simulated surgery, and the like. A procedure plan data structure for live surgeries may be used by the computer-implemented interactive surgical system 100. For example, the procedure plan data structure for live surgeries may be used by surgical hub 106 to enhance situational awareness and/or the operational aspects of the computer-implemented interactive surgical system 100. The procedure plan data structure for live surgeries may be used by the surgical hub 106 to record discrete elements of the live surgery for structured analysis.

A procedure plan data structure may be used by a simulation device 30000. For example, the procedure plan data structure may be used by the simulation device 30000 to establish a setting and/or one or more objectives for a simulation session. For example, the procedure plan data structure may be used by the simulation device 30000 to record the discrete elements of the simulated surgery for structured analysis.

The procedure plan data structure may include any structure suitable for capturing data elements related to the procedure. For example, the procedure plan may be recorded in a tree-like data structure, such as the one shown in FIG. 11A, for example. Here, the root of the tree structure represents the core procedure data 30066. The core procedure data 30066 may include information about the procedure as a whole, such as procedure name, procedure code, patient name, date, time, and the like. For a simulation, the core procedure data 30066 may include information about simulation device, such as device ID, software version, user, the simulation run settings, such as frame rate, resolution, connected user interface devices, and the like.

The procedure data may include leaves of the tree structure. The first level of leaves may include data regarding the main aspects of the procedure plan, such as the procedure setup 30068, one or more procedure stages 30070, one or more contingencies 30072, and the data regarding the result of the procedure 30074.

The setup data 30068 may include information related to the preparations and/or initial state of the procedure. For example, the setup data 30068 may include elements such as staff manifest, staff roles and/or staff IDs, operating room ID, an equipment list, a room layout, an initial surgical table position, a listing of instruments and/or consumables on prepared in the surgical field, any initial settings associated with equipment, pre-surgical imaging, patient record, etc. For a simulation, the setup data 30068 may include information related the simulated environment, such as a record of the simulated anatomy, a record of the simulated physiology, pre-surgical imaging, and the like.

The stage data 30070 may include data elements related to a major milestone of the procedure. For example, a stage of a procedure may include a milestone such as establishing access. The stage data 30070 may include information related to the staff, equipment, technique, and steps that may be used to perform the particular stage of the procedure. The stage data 30070 may include a stage ID.

The stage may be further detailed by one or more sub-leaves, such as one or more surgical tasks 30076. The surgical task may represent a discrete surgical step within a given stage. For example, within the stage of access, placing a trocar may be a surgical task. The surgical task data 30076 may include a task ID. The surgical task data 30076 may include information related to the particular task, such as the staff and/or surgeon performing the task, the equipment to be used, the particular technique being applied, the patient vitals at the time the task is being performed, other environment information, and the list. Each task may be further detailed with goal data 30078, data related to an anatomy-instrument interaction 30080, and result data 30082. The goal data 30078 may include information indicative of the relative success of the task performance. The goal data 30078 may include information about expected task duration, acceptable performance specificity, efficiency modality, avoidance of complications, and the like. The result data 30082 may include information related to one or more goals. The result data 30082 may record the surgical performance (e.g., live and/or simulated) relative to the goals.

The task data 30076 may include one or more elements of anatomy-instrument interaction data 30080. The anatomy-instrument interaction data 30080 may represent a granular indication of surgical performance. The anatomy-instrument interaction data 30080 may represent the one or more specific activities used to perform the surgical task. The anatomy-instrument interaction data 30080 may represent the observable behavior of the surgeon.

In an example, the anatomy-instrument interaction data 30080 may include the specific positions, forces, angles, and the like being applied to the anatomy by the surgeon. For example in a live surgery, data recorded from smart instruments by the surgical hub 106 may be captured as anatomy-instrument interaction data 30080. For example, a smart surgical stapler in cooperation with other elements of the computer-implemented interactive surgical system 100 may record stapler position, angle, tip forces, jaw forces, staple cartridge type, closing pressure, firing rate, and the like. In a simulated surgery, similar data elements may be captured.

The contingency data 30072 may indicate any complications that may be relevant to the procedure. Each contingency data 30072 may include one or more task data elements 30084 that address the appropriate response to the particular complication. The contingency data 30072 may indicate deviations from an original procedure plan. Also for example, contingency data may be cross-referenced to one or more tasks 30078 and/or anatomy-instrument interactions 30080. For example, if a certain performance in an anatomy-instrument interactions 30080 could lead to a complication, the nature of that performance and a cross-reference to the contingency may include in the result data 30082 associated with that anatomy-instrument interactions 30080.

The result data 30074 may be indicative of the result of the procedure. Here overall metrics of the surgical performance may be stored, notes, actual and/or simulated patient recovery information, and/or patient outcomes. For example, the result data 30074 may include efficiency information, cost information, surgical duration, workload metrics, percentage of planned consumables used, and the like.

FIG. 11B illustrates a procedural plan data structure with the above disclosed elements, which further establishes structure of alternative steps for completing a particular procedure, task, or activity. As shown, the procedure represented by the procedure data 30086 may include two alternative setups, each indicated by respective setup data-a first setup data 30088, 30090 and a second setup data 30092. The first setup data 30088, 30090 may include two alternative tasks 30094, 30096. The second setup data 30092 may include one task 30098. In this illustration, the procedure represented by procedure data 30086 may be accomplished in three different ways. First via first setup 30088 and the first task 30094. Second via the first setup 30090 and the second task 30096. And third via the second setup 30092 and its corresponding task 30098.

Each path of the tree structure may represent a particular set of alternative ways to perform the procedure. Such a structure may be useful to aid the creation of a particular procedure plan for a particular live and/or simulated surgery. Such a structure may be useful to simulate many possible alternatives of a procedure to assess the differences in results.

Figure 12:
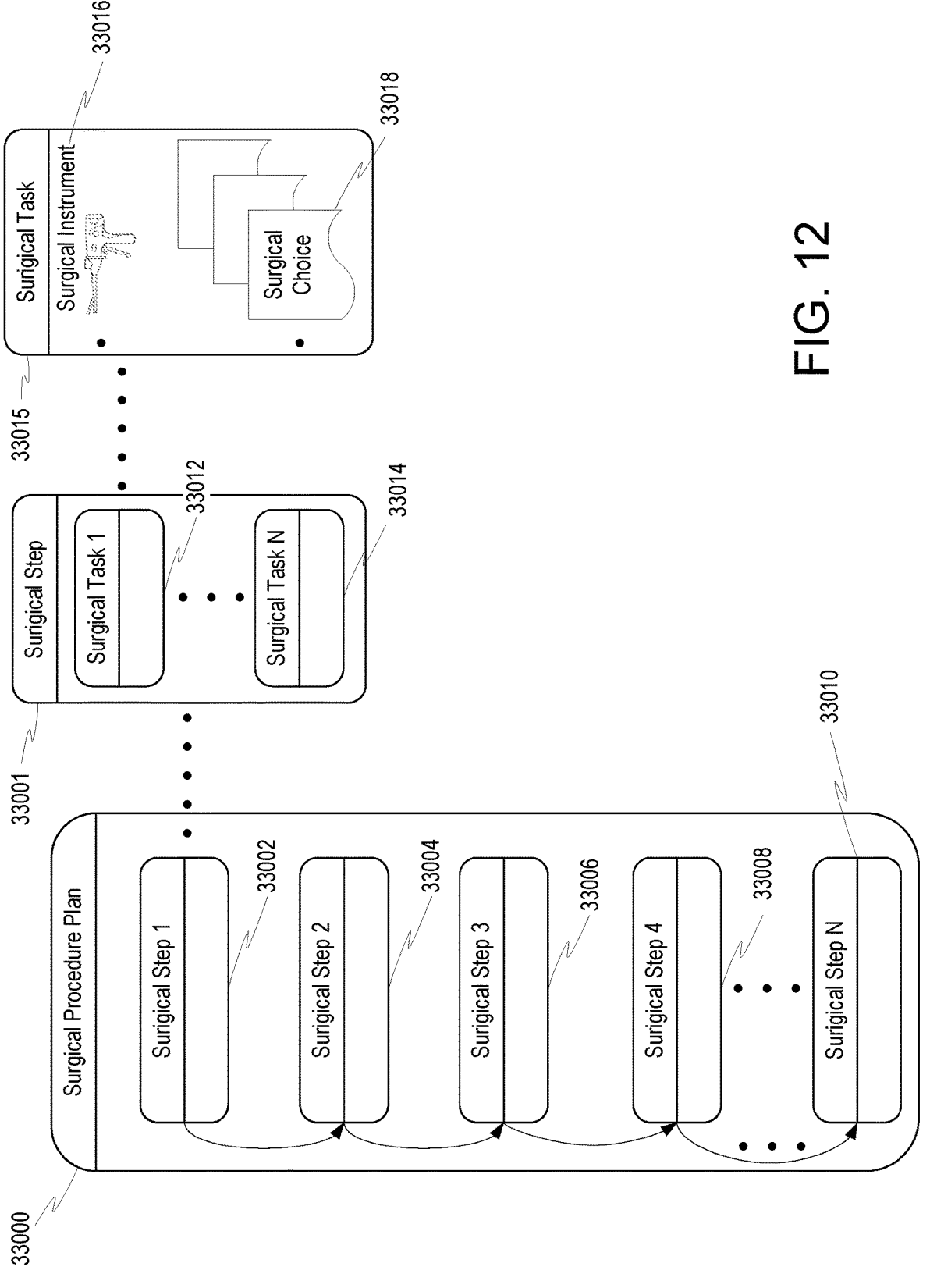
FIG. 12 illustrates an example surgical procedural plan data structures for use with a computer-implemented interactive surgical system and/or a surgical simulator.

FIG. 12 illustrates an example surgical procedural plan 33000 data structures for use with a computer-implemented interactive surgical system and/or a surgical simulator. The computer-implemented interactive surgical system and/or a surgical simulator may be the simulation device 30000 (e.g., described in FIGS. 7 and 8). The surgical procedure plan 33000 may be implemented by the simulation device 30000. The surgical procedure plan 33000 may be implemented by the processor 30034 of the simulation device 30000.

The surgical procedure plan 33000 may include a plurality of surgical steps, such as surgical step 1 (33002), surgical step 2 (33004), surgical step 3 (33006), surgical step 4 (33008), through surgical step N (33010). For example, the surgical procedure plan 33000 may be a surgical procedure plan for a laparoscopic sigmoid colectomy procedure. In such case, the surgical procedure plan 33000 may include the following surgical steps: initiate, access, mobilize colon, resect sigmoid, perform anastomosis, and conclude.

A surgical step may include a plurality of surgical tasks. For example, the surgical step (33001) may include surgical task 1 (33012) through surgical task N (33014). In an example, the surgical step 33001 may be a surgical step "initiate" of the surgical procedure plan 3300 for a laparoscopic sigmoid colectomy procedure. In such case, the surgical step 33001 (33002) may include the following surgical tasks: make incisions, place trocars, and assess adhesions. In an example, the surgical step 33001 may be a surgical step "access" of the surgical procedure plan 3300 for a laparoscopic sigmoid colectomy procedure. In such case, the surgical step 33001 may include the following surgical tasks: dissect adhesions, dissect mesentery, and identify ureter.

A surgical task may include a surgical instrument selection and a plurality of surgical choices. For example, a surgical task 33015 may include a surgical instrument selection 33016 and surgical choices 33018. In an example, surgical task 33015 may be a surgical task of the surgical step "initiate" of the laparoscopic sigmoid colectomy procedure. In such case, the surgical task 33015 may be to make incisions (e.g., for trocar placement). The surgical task 33015 may include a surgical instrument selection 33016 of scalpel. The surgical task 33015 may include a surgical choice 33018 of incision length of 10 mm for a laparoscope port. The surgical task 33015 may include a surgical choice 33018 of incision location of umbilicus for a laparoscope port. The surgical task 33015 may include a surgical choice 33018 of incision length of 5 mm for a grasper port. The surgical task 33015 may include a surgical choice 33018 of incision location of upper right quadrant of abdomen for a grasper port. The surgical task 33015 may include a surgical choice 33018 of incision length of 5 mm for a harmonic energy device port. The surgical task 33015 may include a surgical choice 33018 of incision location of lower right quadrant of abdomen for a harmonic energy device port.

In an example, surgical task 33015 may be a surgical task of the surgical step "access" of the laparoscopic sigmoid colectomy procedure. In such case, the surgical task 33015 may be to dissect mesentery. The surgical task 33015 may include a surgical instrument selection 33016 of grasper. The surgical task 33015 may include a surgical instrument selection 33016 of a harmonic energy device. The surgical task 33015 may include a surgical choice 33018 of performing dissection in the direction of medial-to-lateral. The surgical task 33015 may include a surgical choice 33018 of performing dissection in the direction of lateral-to-medial.

Figure 13:
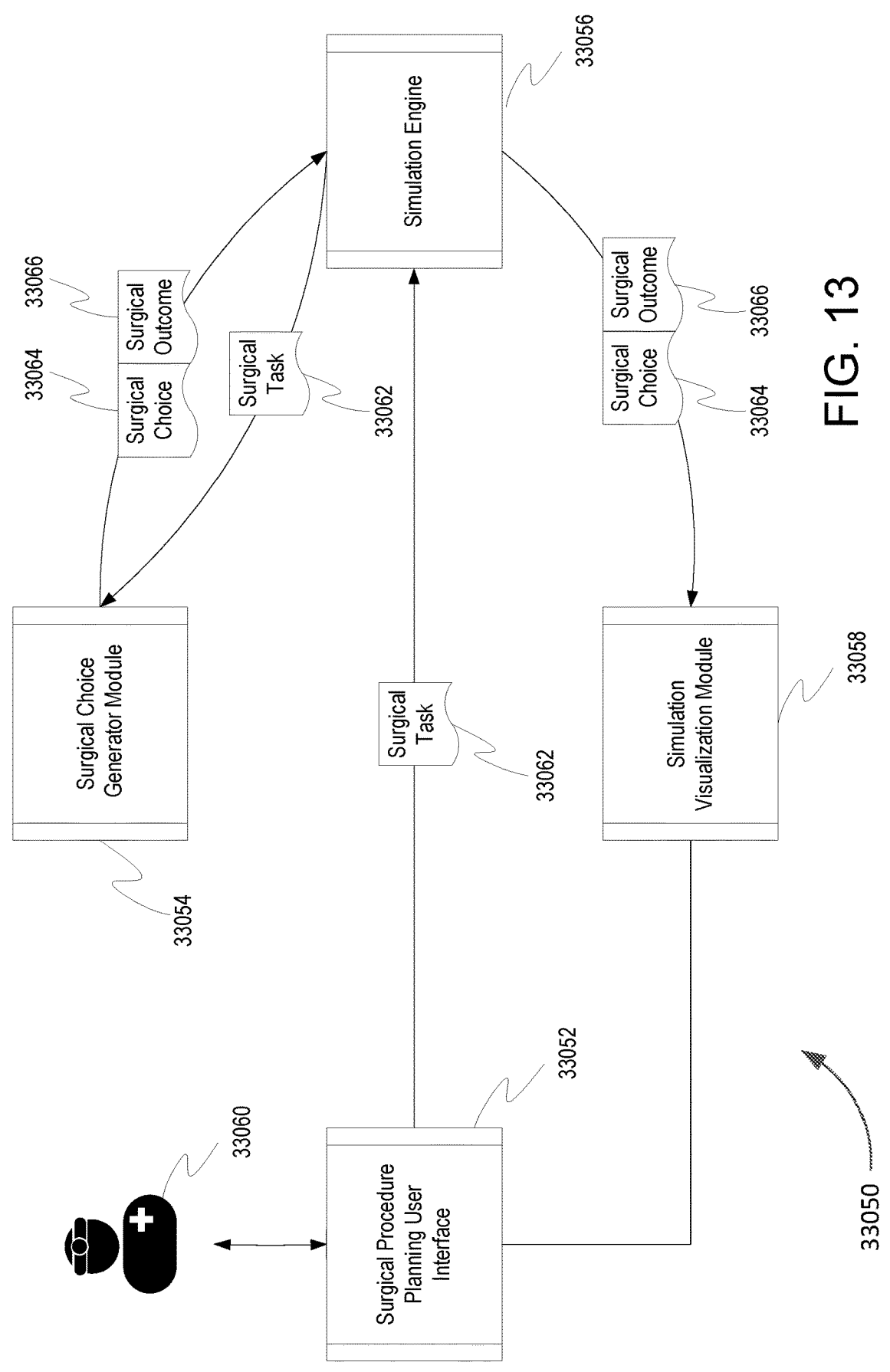
FIG. 13 illustrates an example data flow of simulation-assisted surgical procedure planning.

FIG. 13 illustrates an example data flow 33050 of simulation-assisted surgical procedure planning. The data flow 33050 may be performed by the simulation device 30000 (e.g., described in FIGS. 7 and 8). The data flow 33050 may be performed by the processor 30034 of the simulation device 30000.

A surgeon 33060 may use a surgical procedure planning user interface 33052 to create a surgical procedure plan. For example, the surgeon 33060 may create a surgical procedure plan (e.g., surgical procedure plan 33000 as described in FIG. 12) for a laparoscopic sigmoid colectomy procedure.

The surgical procedure planning user interface 33052 may retrieve a surgical procedure plan template and present the surgical procedure plan template to the surgeon 33060. The surgical procedure plan template may include a plurality of pre-defined surgical steps and each surgical step may include a plurality of pre-defined surgical tasks. For example, the surgical procedure plan template may be a template for a laparoscopic sigmoid colectomy procedure. The plurality of pre-defined surgical steps in the template may be the following surgical steps as described in the surgical procedure plan 33000: initiate, access, mobilize colon, resect sigmoid, perform anastomosis, and conclude.

The surgeon 33060 may select a surgical task within a surgical step for which to simulate surgical choices. For example, the surgeon 33060 may select surgical task "make incisions". In response to the selection, the surgical procedure planning user interface 33052 may send the surgical task selection 33062 of "make incisions" to a simulation engine 33056.

In response to the surgical task selection 33062 of "make incisions", the simulation engine 33056 may send the selection 33062 to a surgical choice generator module 33054 for generation of surgical choices to simulate. In response to the selection 33062, the surgical choice generator module 33054 may generate one or more surgical choices for making incisions for trocar placement (e.g., as further described in FIGS. 14A-B and FIGS. 15A-B) and corresponding surgical outcomes.

Figures 14A, 14B:
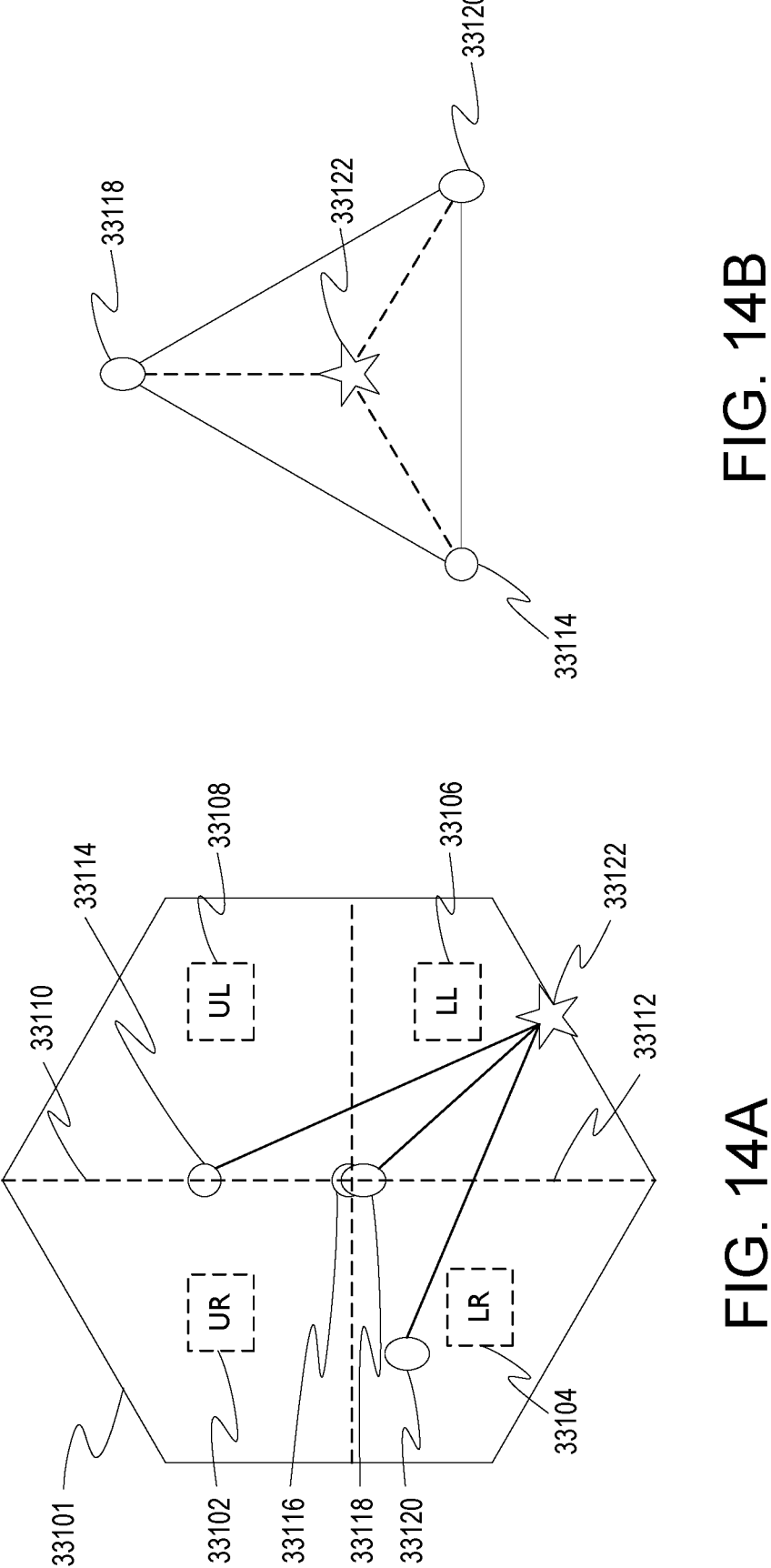
FIGS. 14A and 14B illustrate an example set of surgical choices for a surgical task for use with a computer-implemented interactive surgical system and/or a surgical simulator.

FIG. 14A and FIG. 14B illustrate an example set of surgical choices for a surgical task for use with a computer-implemented interactive surgical system and/or a surgical simulator. The computer-implemented interactive surgical system and/or a surgical simulator may be the simulation device 30000 (e.g., described in FIGS. 7 and 8). The example set of surgical choices may be implemented by the simulation device 30000. The example set of surgical choices may be implemented by the processor 30034 of the simulation device 30000.

As shown in FIG. 14A, a shape 33101 represents the abdomen of a patient's front. The shape 33101 is divided into upper right quadrant (UR) 33102, upper left quadrant (UL) 33108, lower right quadrant (LR) 33104, and lower left quadrant (LL) 33106, with umbilicus 33116 in the center. A midline consisting of an upper midline 33110 and a lower midline 33112 divides the shape 33101 into equal left and right halves. An oval shape 33118 overlapping with umbilicus 33116 represents a location of an 12 mm incision for a laparoscope's trocar port. An oval shape 33120 in the LR area represents a location of a 12 mm incision for a harmonic energy device's trocar port. A circle shape 33114 on the upper midline 33110 represents a location of a 5 mm incision for a grasper's trocar port. A star shape 33122 represents a location of a target anatomy (e.g., sigmoid colon in a laparoscopic sigmoid colectomy). 33118, 33120, 33112 represent surgical choices of incision location for an incision for a trocar port. Solid lines between 33120 and 33122, between 33118 and 33122, between 33114 and 33122 represent the spatially relationships among the laparoscope, the harmonic device, the grasper when the three of them are all pointed at the target anatomy 33122 during a surgical procedure. Such spatial relationships represent a spatial arrangement of laparoscope and two surgical instruments that provide sufficient visibility of the surgical instruments as the three of them are working on the target anatomy. Such arrangement may be referred to as "triangulation" by a person skilled in the art.

FIG. 14B shows a field-of-view perspective of the spatial relationships among the laparoscope, the harmonic device, and the grasper when the three of them are all pointed at the target anatomy 33122 during a surgical procedure. As such, the sight of the harmonic device and the sight of the grasper are maximized when the three of them are both pointed at and working on the target anatomy 33122 during a surgical procedure.

Figure 15B:
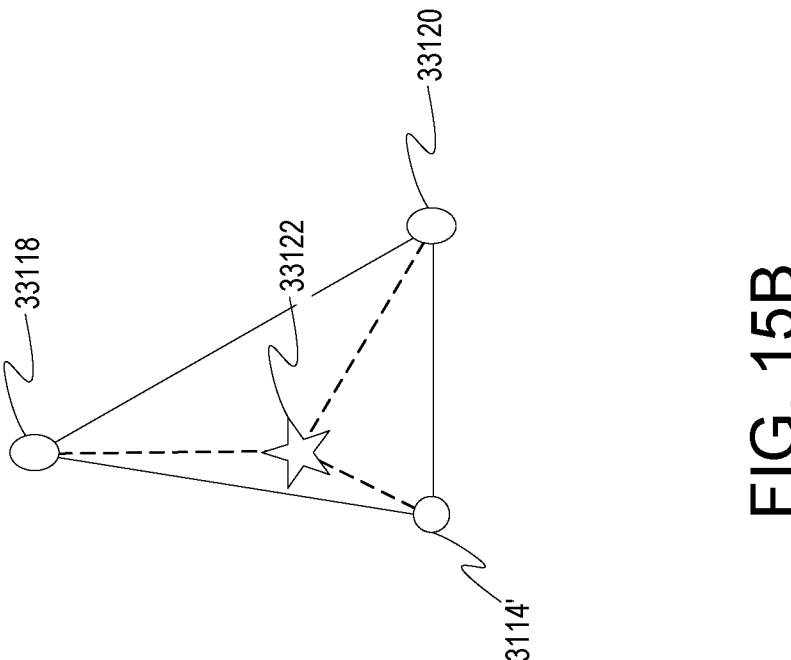
FIGS. 15A and 15B illustrate an example set of surgical choices for a surgical task for use with a computer-implemented interactive surgical system and/or a surgical simulator.
Figure 15A:
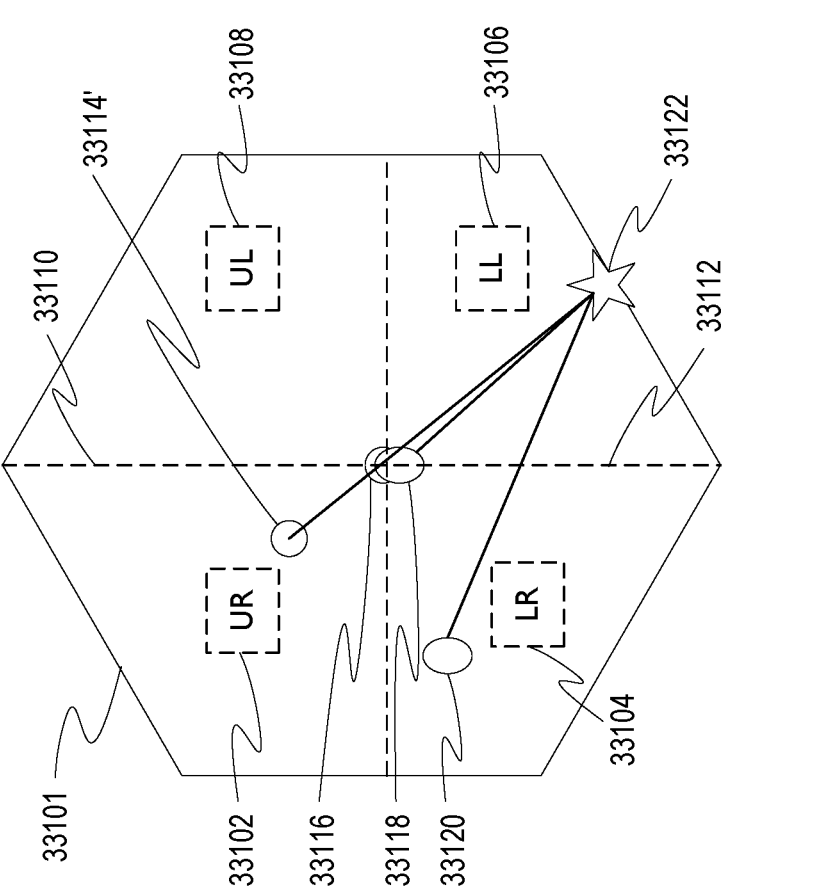

FIG. 15A and FIG. 15B illustrate an example set of surgical choices for a surgical task for use with a computer-implemented interactive surgical system and/or a surgical simulator. The computer-implemented interactive surgical system and/or a surgical simulator may be the simulation device 30000 (e.g., described in FIGS. 7 and 8). The example set of surgical choices may be implemented by the simulation device 30000. The example set of surgical choices may be implemented by the processor 30034 of the simulation device 30000.

FIG. 15A illustrates the same surgical choice of an incision location for a laparoscope's trocar port as illustrated in FIG. 14A, the same surgical choice of an incision location for a harmonic device's trocar port as illustrated in FIG. 14A, and a different surgical choice of an incision location for a grasper 33114' from that is illustrated in FIG. 14A. FIG. 15B shows a field-of-view perspective of the spatial relationships among the laparoscope, the harmonic device, and the grasper when the three of them are all pointed at the target anatomy 33122 during a surgical procedure. As such, the sight of the grasper is significantly limited due to the close proximity of 33114' to 33122 and 33118 spatially.

Referring to FIG. 13, the surgical choices 33064 of incision locations shown in FIGS. 14A-B may be generated by the surgical choice generator module 33054 and sent to the simulation engine 33056. A surgical outcome 33066 corresponding to the surgical choices 33064 may also be sent by the module 33054. In such case, the surgical outcome 33066 may be "no surgical complication". A "no complication" surgical outcome may indicate no surgical complication results from the surgical choices 33064.

The surgical choices 33064 of incision locations shown in FIGS. 15A-B may be generated by the surgical choice generator module 33054 and sent to the simulation engine 33056. A surgical outcome 33066 corresponding to the surgical choices 33064 may also be generated by the module 33054. Such surgical outcome 33066 may be a surgical complication that the incision location 33114' for the grasper port 33114' is aborted and the incision is closed (e.g., due to the limited sight of the grasper).

The simulation engine 33056 may send the surgical choices 33064 of incision locations shown in FIGS. 14A-B and FIGS. 15A-B and the corresponding surgical outcomes 33066 to a simulation visualization module 33058. The simulation visualization module 33058 may be integrated into the surgical procedure planning user interface 33052 or separate from the user interface 33052. In response, the surgical procedure planning user interface 33052 may visualize the simulation of the surgical choices 33064 of incision locations and the corresponding surgical outcomes 33066, e.g., in an automated process. The automated process may visualize the surgical choices 33064 of incision locations shown in FIGS. 14A-B and the corresponding surgical outcome 33066 of "no surgical complication" and continue to visualize the surgical choices 33064 of incision locations shown in FIGS. 15A-B and the corresponding surgical outcome 33066 of the surgical complication described herein.

In response to the visualization of the surgical choices 33064 of incision locations and the corresponding surgical outcomes 33066, the surgeon 33060 may select the surgical choices 33064 of incision locations shown in FIGS. 14A and 14B. In such case, the surgical procedure planning user interface 33052 may store such surgical choices of incision locations under the surgical task of "make incisions" that is a part of the surgical step "initiate" of a surgical procedure plan 33000 for a laparoscopic sigmoid colectomy. The surgeon 33060 may not select the surgical choices 33064 of incision locations shown in FIGS. 15A and 15B (e.g., due to the surgical complications described). In such case, the surgical procedure planning user interface 33052 may discard such surgical choices. In such matter, the remaining surgical steps, surgical tasks, and surgical choices may be generated for the surgical procedure plan 33000 for a laparoscopic sigmoid colectomy.

Referring now to the surgical choice generator module 33054, the module 33054 may generate surgical choices 33064 and corresponding surgical outcomes 33066 based on the given surgical task 33062 using machine learning models.

For example, a generative machine learning model may be trained using past pre-surgical data and/or past surgical procedure data in a remote system (e.g., the cloud 17 as described in FIG. 1 and the remote system 31008 as described in FIG. 15). The generative machine learning model may be any suitable generative model, such as generative adversarial networks (GANs) or a Markov chain-based model.

For example, a machine learning model based on GANs (GANs model) may be trained using past surgical procedure data from laparoscopic sigmoid colectomy procedures. The GANs model may model that data pattern that given a surgical step, a list surgical tasks may be performed. The GANs model may model the probability distribution of the surgical tasks present in the past surgical procedure data. That is, when the GANs model generates a surgical task from the list of possible surgical tasks, the surgical task is generated at a probability according to the probability distribution. In an example, the GANs model may generate a surgical task of making incisions for trocar placement for surgical step "initiate" at a probability of 100% because all laparoscopic sigmoid colectomy procedures start with such surgical task.

Similarly, the GANs model may model the data pattern that given a surgical task, a list of surgical choices may be made. The GANs model may model the probability distribution of the surgical choices present in the past surgical procedure data. That is, when the GANs model generates a surgical choice from the list of possible surgical choices given a surgical task, the surgical choice is generated at a probability according to the probability distribution. In an example, the GANs model may generate a surgical choice, e.g., a surgical choice of a laparoscope's trocar port's incision location at the umbilicus, at a probability of 95% because it may be a standard technique for a laparoscopic sigmoid colectomy procedure and reflected in the past surgical procedure data for laparoscopic sigmoid colectomy procedures.

Similarly, the GANs model may model the data pattern that given a surgical choice, one or more surgical outcomes may follow. The GANs model may model the probability distribution of the surgical outcomes present in the past surgical procedure data. That is, when the GANs model generates a surgical outcome from the list of possible surgical outcomes given a surgical outcome, the surgical outcome is generated at a probability according to the probability distribution. In an example, the GANs model may generate a surgical outcome of "surgical complication", e.g., for a surgical choice of a harmonic device trocar port's incision location being at the lower left quadrant of the abdomen, at a probability of 90%. Such probability of a surgical complication may be due to the significantly limited sight of the harmonic device in laparoscope's view regardless of the incision location for a grasper.

As such, the GANs model may generate a surgical choice or a surgical outcome with an associated probability. For example, when the surgical choice generator module 33054 generates a surgical choice using the GANs model, the module 33054 may generate a surgical choice 33064 and a corresponding surgical outcome 33066 with an associated probability. The simulation engine 33056 may send the surgical choice 33064 and the corresponding surgical outcome 33066 with the associated probability to the simulation visualization module 33058. In response, the surgeon 33060 may view the surgical choice 33064 and the corresponding surgical outcome 33066 in the context of its probability. In an example, a high probability of a negative surgical outcome may dissuade the surgeon 33060 from selecting the associated surgical choice. In an example, a low probability of a negative surgical outcome may not be singly determinative of whether the surgeon 33060 may select the associated surgical choice. For example, the surgeon 33060 may simulate other surgical choices to review if their corresponding surgical outcomes may be negative and if so whether their probabilities are higher or lower before selecting which surgical choice to add to the surgical procedure plan.

Figure 16:
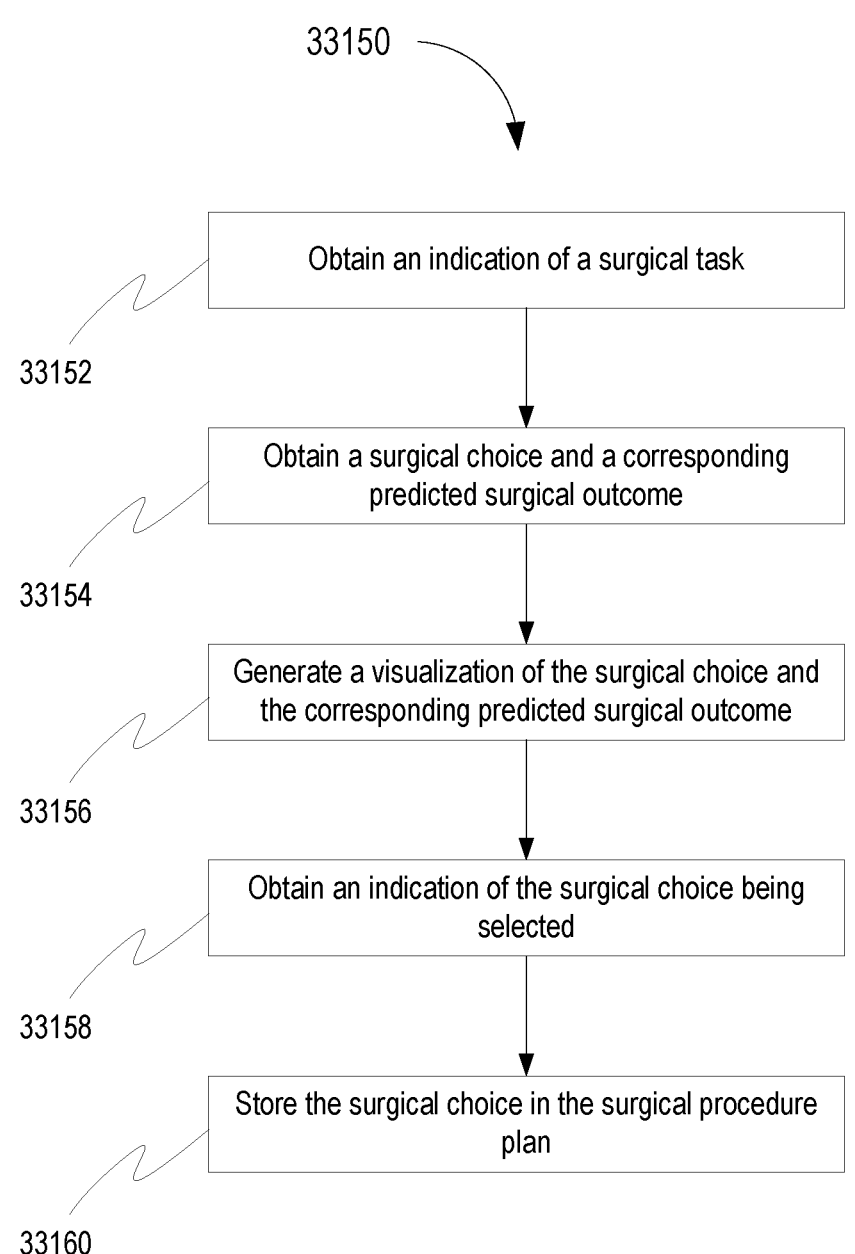
FIG. 16 is a flow chart of an example operation of simulation-assisted surgical procedure planning.

FIG. 16 is a flow chart 31150 of an example operation of simulation-assisted surgical procedure planning. For example, the example operation may include a process to determine a surgical choice and a corresponding surgical outcome to perform a simulated surgical task in a simulated environment. The process may store a selected surgical choice and a selected corresponding surgical outcome in a surgical procedure plan.

At 33152, an indication of a surgical task may be obtained. The surgical task may be associated a surgical step of a surgical procedure plan. For example, the indication of the surgical task may be obtained from a surgical procedure planning user interface. For example, the indication of the surgical task may include identifying information of the surgical procedure plan, identifying information of the surgical task, and/or identifying information of the surgical step.

At 33154, a surgical choice and a corresponding predicted surgical outcome may be obtained. The surgical choice and the corresponding predicted surgical outcome may be associated with the surgical task. For example, a machine learning (ML) model may be trained using data of a plurality of past surgical procedures. The ML model may generate the surgical choice and the corresponding predicated surgical outcome using the ML model. The surgical choice and the corresponding predicted surgical outcome may be obtained from the ML model.

At 31156, a visualization of the surgical choice and the corresponding predicted surgical outcome in a simulated environment may be generated.

At 33158, an indication of the surgical choice being selected may be obtained.

At 33160, the surgical choice in the surgical procedure plan may be stored. For example, the surgical choice may be a first surgical choice and the corresponding predicted surgical outcome may be a first corresponding predicted surgical outcome. A second surgical choice and a second corresponding predicated surgical outcome may be obtained. The second surgical choice and the second corresponding predicted surgical outcome may be associated with the surgical task. A visualization of the second surgical choice and the second corresponding predicted surgical outcome may be generated in the simulated environment. An indication of the second surgical choice being not selected may be obtained. The second surgical choice may be discarded.

Surgical procedure planning (e.g., including tool setup) may be based on simulation (e.g., automated simulation runs).

A surgical procedure planning system may be integrated with an artificial intelligence (AI) driven simulation system to visualize surgical steps and anticipated outcomes for a chosen surgical procedure plan and chosen surgical steps. The surgical procedure planning system may assist a user in assembling a surgical procedure plan and running multiple iterations of simulations to identify aspects of the plan that lead to variable outcomes or complications to show both options and the range of results of the assembled plan. The automated simulation may include probability range results from an aggregated set of procedures and outcomes.

The aggregated set of procedures and outcomes may be resulting from previous local surgeries of the user or the facility. The aggregated set of procedures and outcomes may be a larger set from a remote system or a cloud server which has aggregated regional or would-wide datasets. The surgical procedure planning system may include a digital interface. The digital interface may allow a surgeon to choose and plan surgical steps and step through the possible outcomes, including information of the likelihood of an outcome or result, and why. The results shown may include the steps, reasons, complications, etc. that are the highest probable source of the results. The results may be of the entire plan, a step of the plan or a predefined patient complication to the plan. The digital interface may display mitigation that may be used to minimize or maximize results with differing choices.

Operating room setup simulations may be performed with adaptable variables for instruments, equipment, approach, and room aspects.

Equipment needs and instrument needs may be simulated based on a surgical procedure plan (e.g., for a patient) and compared with the surgical procedure plan. Examples of equipment may be C-arm or ultra-sound. The simulation of equipment needs and/or instrument needs and the procedure plan may be compared to determine if all the equipment and/or instruments needed for the procedure are included in the surgical procedure plan. An AI-based simulation may look through all the options of the surgical procedure steps and the associated instruments and tools to determine the equipment and/or instrument needs. The simulation may highlight any issues or other combinations of instruments that may be swapped for the instruments that have been included in the surgical procedure plan.

Robot configuration, setup and steps for hybrid and/or complete robot surgeries may be simulated based on a surgical procedure plan to determine different robot supplementations of a surgeon. Patient positioning on an operating table maybe simulated. Operating table configuration may be simulated. Examples of operation table configuration may be tilt, leg board positions or removal, or bed slide to main column for C-arm or O-arm. Bar configuration may be simulated. Examples of bar configuration may be tilt, up or down, or slide. Arm configuration may be simulated. Examples of arm configuration may be stowed or deployed, or arm positions on bar. Arm to cannula configuration may be simulated. Arm to natural orifice configurations may be simulated. For example, no cannula, such as uManip, gastrointestinal (GI) scope, or cStapler, may be used in the simulation. Arm to perc access configurations may be simulated. For example, no cannula, such as liver retractor, may be used in the simulation. Actions of the surgeon may be automated in the simulation. For example, the simulation may simulate breaking out key steps with variations. Setups such as the following may be simulated: port placements, arm placements, bar or robot, or parking spots of other cart-based robots. Actions of other assistants in certain steps of a procedure may be automated in the simulation. The simulation may be based on statistical sampling of port placements, e.g., to assign optimized positioning for key surgical steps.

The simulator may simulate tool-tissue interaction to avoid tissue-manipulation errors. FIG. 17 illustrates a machine learning-assisted simulation process 33170 for avoiding tissue-manipulation errors.

Surgeon location and relocations needed relative to a patient's orientation and/or positioning for completion of a surgical procedure may be simulated based on a surgical procedure plan. The simulation may identify drive-up robots to supplement single surgeon access. The simulation may simulate multiple options of repositioning of the access of the robot or the lap positing via virtual reality (VR) room visualization. The simulation may simulate organ access implicated by instruments of different lengths. The simulation may simulate and determine a needed patient setup, e.g., robot arm under leg for hysterectomy or endoscopic colon assisted lap. The simulation may simulate port placement and associated implications. FIG. 18 illustrates an example process 33180 of determining optimality of patient specific port placement for an overall surgical procedure.

The simulation may automate understanding of the implications of how the OR may be set up, e.g., how the OR setup may achieve reach, access, all steps of procedure. The simulator may communicate back to OR staff the probability of a setup being successful to outcomes. The simulation system may run through multiple differing runs to determine all of the possible combinations of the equipment, its location, and the efficiency of that placement. The variation may be displayed out to provide the choices the staff has for the options and the implications of each of the options.

The simulator may run simulations to determine patient body and/or limb positioning to minimize setup time or patient injury while providing the best access to a surgical site with the least amount of repositioning. Prior to a surgery a patient may be transferred to the operating table. The final position of the patient may be important and may require planning and coordination by the OR team. Such planning and coordination may require time prior to the surgery and may cause delays during surgery to stop and reposition. For example, simulations may be used to train the staff based on patient characteristics and/or profile, procedure type, room layout, and/or equipment position. The simulator may provide information to the OR team of the optimal position of the patient on the bed to reduce the setup time by not requiring the OR team to plan and may coordinate and direct focus to other tasks. The simulator may provide details to the user on the proper placement and/or position to have least impact to the patient based on condition, and/or when proper placement was met. During surgery prevention of injury may require proper positioning of the patient throughout the surgery. A range of injuries may occur when a patient has been placed or moved improperly during surgery. There may be a set number of diagnoses that may come from such a situation. For example, simulations may be used to teach staff of cues or identifiers of when patient should be moved and how to move them to prevent injury. Examples of common injuries may be Ulnar nerve, Brachial plexus, and Spinal cord. Feedback of divergence from best or trained practice in positioning may be used to baseline the simulator.

The simulation may identify potential issues and options for resolution or changing outcomes. The simulator may identify deviations and/or recovery options from a surgical procedure plan and pre-operative simulations. The simulator may generate notification(s) of the identified deviations and/or recovery options. The simulation may employ virtual geofencing, e.g., for highlighting when surgical action is off preplanned simulation. The simulation may employ mechanical geofencing, e.g., for creating mechanical drive boundary when surgical action is off preplanned simulation. The simulation may provide feedback during approach. The feedback may be via geofencing of critical structures and/or adaptation during action.

The simulator may employ reactive simulation with integrated potential complications and issues for procedural and approach development. For example, new approaches may be developed by HCPs and hospitals, using existing instruments (e.g., IE, novel port positioning, hybrid use of assistant with/without devices), e.g., for procedural development. For example, procedural development may be unique to patient, e.g., how to take clinical inputs (e.g., tumor location, adhesions) into consideration.

Predictive modeling may be employed in simulations. Critical surgical actions for a given procedure may be simulated to develop predictive models (e.g., machine learning models). Predictive models developed for the surgical actions may be employed in surgical procedures that include the surgical actions. A machine learning (ML) model may be employed to identify the stage of a surgical procedure so that the appropriate ML model for a surgical action may be invoked to perform predictions based on localized behaviors observed in simulations. FIG. 19 illustrates an example process 33190 of detecting deviations from expected practice using ML-assisted simulation.

Figure 20:
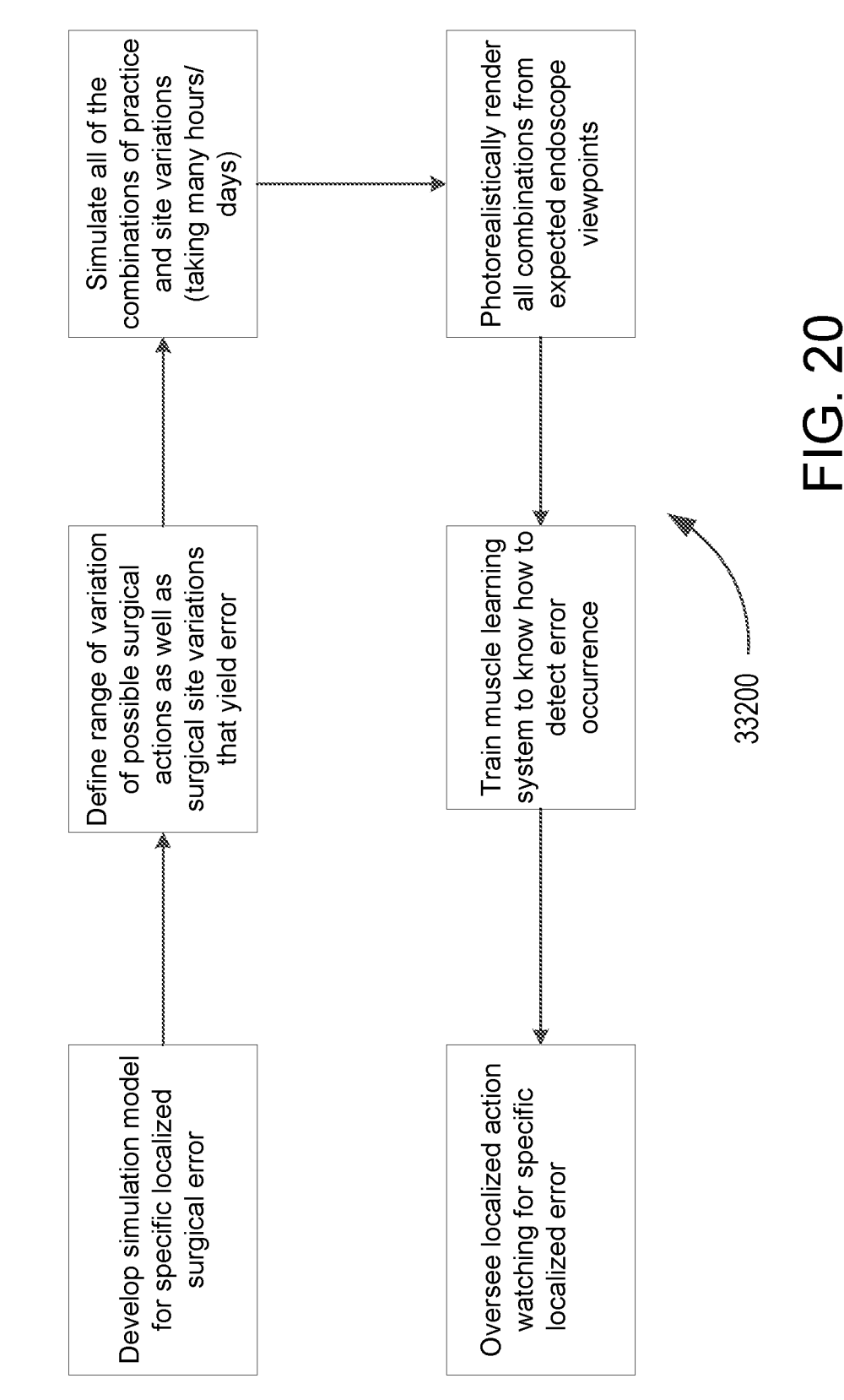
FIG. 20 illustrates an example process of detecting surgical errors using ML-assisted simulation.

Critical surgical errors for a given procedure may be simulated to develop predictive models (e.g., ML models). Predictive models developed for the surgical errors may be employed in surgical procedures that include the surgical errors. A ML model may be employed to identify the stage of a surgical procedure so that the appropriate ML model for a surgical error may be invoked to perform predictions based on localized errors at that stage. FIG. 20 illustrates an example process 33200 of detecting surgical errors using ML-assisted simulation.

Simulations may be performed pre-operatively to assess and/or optimize patient outcomes based on patient input. The simulations may provide indication and/or notification of most likely complications or adjustments within an impending surgical procedure to alert surgeon and/or staff and/or facility. For example, patient data, and/or patient vitals and/or patient physical characteristics may be used as inputs for simulations prior to a surgical procedure. The simulations may represent a realistic training and/or preparation prior to the surgical procedure. For example, patients' pre-operative data and/or patients' vitals and/or patients' physical characteristics may be inputted back into the simulator to identify any changes and/or modifications to be made and may provide notification(s) of the changes and/or modifications to an OR team, e.g., through an app and/or monitor and/or message. The changes and/or modifications may minimize complications and/or optimize efficiency within the OR. In an example, pre-surgery check may occur up to two weeks in advance, factors such as the following may change within that time period that may impact patient outcomes and/or approaches the surgeon takes: blood pressure, heart rate, or breathing changes. Real-time information of such factors may be added to the previous simulator runs to indicate recommendations to improve outcomes. For example, changes in pre-surgery checkup verses pre-op inputs baselined against gold standards or facility procedures to provide notifications, changes, and/or optimization to modify and/or adjust facility influencers for better outcomes and optimization on efficiencies. Identification of operating room may be diverted based on equipment or room layout, the staff location within the room, the staff skill set or experience required, based on the changes and/or impact of complication(s) to improve outcomes, and based on knowing when and/or how to react. Identifying when additional staff and/or resources are needed. In an example, additional scrub and/or circulating nurse, and/or additional specialty surgeon on standby may be needed. In an example, if surgery was for cholecystectomy and patient showed possible lung or heart issues then a Pulmonologist or Cardiologist may be on standby if complications were to arise.

The simulator may display and may provide review of automated simulation(s) with feedback, recommendations, and/or alternatives highlighted for a simulation user. For example, the simulator may display and may provide review of automated surgical step operation based on a setup and/or or configurations. The simulator may highlight when the automated surgical step operation does not work. The simulator may compare the automated result to real-world and/or human operated options. The simulator may show key differences from the comparison. The simulator may learn options for the surgical step from automation. The simulator may obtain feedback on the options for the surgical step from a simulator user (e.g., a surgeon). The simulator may indicate which earlier setup steps may result in later steps having robotic and/or patient collisions and/or access limitations.

The simulator may predicate and communicate the probability of a surgeon's skill being able to achieve success given simulation of setup and patient parameters. The surgeon's skill may be from earlier training run inputs and/or from CSATS scores. Statistics may be created based on a plurality of simulation runs from a plurality of surgeons. The statistics may be used to build a database. The simulation may predict outcomes based on the procedure, the difficulty of the procedure, its plan, the approaches and the surgeon skill. The simulation may predict setup shortfalls and/or where the setup shortfalls may be in the setup and/or what outcome the setup shortfalls affect. The simulation may highlight tasks that are more challenging for the surgeon based on previous simulation runs of recorded skill level and may make recommendations to lower the difficulty of the task or may suggest alternative approaches, access locations, and/or instrument mixes that would improve the outcomes, e.g., including hybrid or full robotics.

Simulation OR efficiency behaviors and/or boundaries may be performed to refine boundaries and/or notifications from a surgical data system (e.g., a surgical hub). Data captured from using the simulator may be used to model and/or identify the extent of contamination and/or size of the exposure zone of highly contagious infections. Such information may be communicated to the monitoring systems (e.g., to control/direct patients). For example, the Covid pandemic created new situations for hospital facilities in which the hospital facilities were not prepared. The simulator may be used to determine one or more methods for how a facility may handle the flow of incoming patients to minimize infection to the facility. For example, the Covid pandemic created new situations in which varying array of symptoms were displayed by individuals differently. The simulator may identify and/or capture symptoms and may provide the facility a checklist of signs to look for. The simulator may communicate to the facility monitoring system for incoming patients to direct them to a controlled environment to minimize the potential contamination and/or infection to the facility.

The invention claimed is:

1. A computing device for generating a surgical procedure plan via surgical simulation, the computing device comprising:
    a processor configured to:
        obtain an indication of a surgical task, wherein the surgical task is associated with a surgical step of the surgical procedure plan;
        obtain a surgical choice, wherein the surgical choice is associated with the surgical task;
        determine a surgeon-based tool-tissue simulation that avoids a surgical error, wherein the surgeon-based tool-tissue simulation is based on the surgical choice, a surgical experience level, and a surgical workload;
        determine an infection exposure simulation for a room layout;
        determine a predicted surgical outcome based on the surgeon-based tool-tissue simulation, the infection exposure simulation, and a surgical setup data, wherein the surgical setup data comprises the room layout, a staff layout, and a patient position, wherein the patient position minimizes injury to a patient, and wherein the staff layout indicates at least a location of a staff member;
        generate a visualization of the surgical choice and the predicted surgical outcome using a simulated environment;
        obtain an indication confirming the surgical choice as being selected; and
        store the surgical choice in the surgical procedure plan.

2. The computing device of claim 1, wherein the indication of the surgical task is obtained from a surgical procedure planning user interface.

3. The computing device of claim 1, wherein the indication of the surgical task comprises identifying information of the surgical procedure plan, identifying information of the surgical task, and identifying information of the surgical step.

4. The computing device of claim 1, wherein the surgical task comprises a task that contributes to a completion of the surgical step of the surgical procedure plan.

5. The computing device of claim 1, wherein the processor is further configured to train a machine learning (ML) model using data from at least a surgical procedure.

6. The computing device of claim 1, wherein the surgical choice is a first surgical choice, wherein the predicted surgical outcome is a first corresponding predicted surgical outcome, wherein the visualization is a first visualization, and wherein the processor is further configured to:
    obtain a second surgical choice, wherein the second surgical choice is associated with the surgical task;
    determine a second predicted surgical outcome based on the second surgical choice and the surgical setup data; and
    generate a second visualization of the second surgical choice and the second predicted surgical outcome in the simulated environment.

7. The computing device of claim 1, wherein the processor is further configured to determine a machine learning (ML) model, wherein the ML model is associated with data from at least a surgical procedure.

8. The computing device of claim 7, wherein the processor being configured to determine the predicted surgical outcome further comprises the processor being configured to determine the predicted surgical outcome based on the surgeon-based tool-tissue simulation, the infection exposure simulation, the surgical setup data, and the ML model.

9. A computer-implemented method for generating a surgical procedure plan via surgical simulation, the method comprising:
    obtaining an indication of a surgical task, wherein the surgical task is associated with a surgical step of the surgical procedure plan;
    obtaining a surgical choice, wherein the surgical choice is associated with the surgical task;
    determining a surgeon-based tool-tissue simulation that avoids a surgical error, wherein the surgeon-based tool-tissue simulation is based on the surgical choice, a surgical experience level, and a surgical workload;
    determining an infection exposure simulation for a room layout;
    determining a predicted surgical outcome based on the surgeon-based tool-tissue simulation, the infection exposure simulation, and a surgical setup data, wherein the surgical setup data comprises the room layout, a staff layout, and a patient position, wherein the patient position minimizes injury to a patient, and wherein the staff layout indicates at least a location of a staff member;
    generating a visualization of the surgical choice and the predicted surgical outcome using a simulated environment;
    obtaining an indication confirming the surgical choice as being selected; and
    storing the surgical choice in the surgical procedure plan.

10. The computer-implemented method of claim 9, wherein the indication of the surgical task is obtained from a surgical procedure planning user interface.

11. The computer-implemented method of claim 9, wherein the indication of the surgical task comprises identifying information of the surgical procedure plan, identifying information of the surgical task, and identifying information of the surgical step.

12. The computer-implemented method of claim 9, wherein the surgical task comprises a task that contributes to a completion of the surgical step of the surgical procedure plan.

13. The computer-implemented method of claim 9, further comprising:

training a machine learning (ML) model using data from at least a surgical procedure.

14. The computer-implemented method of claim 9, wherein the surgical choice is a first surgical choice, wherein the predicted surgical outcome is a first corresponding predicted surgical outcome, wherein the visualization is a first visualization, and wherein the method further comprises:

obtaining a second surgical choice, wherein the second surgical choice is associated with the surgical task;

determining a second predicted surgical outcome based on the second surgical choice and the surgical setup data; and generating a second visualization of the second surgical choice and the second predicted surgical outcome in the simulated environment.

15. The computer-implemented method of claim 9, wherein the method further comprises determining a machine learning (ML) model, wherein the ML model is associated with data from at least a surgical procedure.

16. The computer-implemented method of claim 15, wherein determining the predicted surgical outcome further comprises determining the predicted surgical outcome based on the surgeon-based tool-tissue simulation, the infection exposure simulation, the surgical setup data, and the ML model.

\* \* \* \* \*